(12) United States Patent
Zhou

(10) Patent No.: US 8,815,515 B1
(45) Date of Patent: Aug. 26, 2014

(54) METHODS, COMPOSITIONS, AND KITS FOR RARE ALLELE DETECTION

(75) Inventor: Luming Zhou, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 335 days.

(21) Appl. No.: 12/890,041

(22) Filed: Sep. 24, 2010

(51) Int. Cl.
*C12Q 1/68* (2006.01)
*C12P 19/34* (2006.01)

(52) U.S. Cl.
USPC .......................... 435/6.12; 435/6.1; 435/6.11

(58) Field of Classification Search
CPC ........................... C12Q 1/6827; C12Q 1/6858
See application file for complete search history.

(56) References Cited

U.S. PATENT DOCUMENTS

| | | | |
|---|---|---|---|
| 5,723,591 | A | 3/1998 | Livak et al. |
| 5,866,336 | A | 2/1999 | Nazarenko et al. |
| 6,037,130 | A | 3/2000 | Tyagi et al. |
| 6,150,097 | A | 11/2000 | Tyagi et al. |
| 6,174,670 | B1 | 1/2001 | Wittwer et al. |
| 6,277,607 | B1 | 8/2001 | Tyagi et al. |
| 7,387,887 | B2 | 6/2008 | Wittwer et al. |
| 7,582,429 | B2 | 9/2009 | Wittwer et al. |

FOREIGN PATENT DOCUMENTS

| | | | |
|---|---|---|---|
| WO | WO 2007106534 A2 * | 9/2007 | |
| WO | WO2008109823 A2 | 9/2008 | |
| WO | WO 2008109823 A2 * | 9/2008 | |
| WO | WO2010054254 A1 | 5/2010 | |

OTHER PUBLICATIONS

Gibson, N.J., "The use of real-time PCR methods in DNA sequence variation analysis," Clinica Chimica Acta, 2006, vol. 363, pp. 32-47.*
Gibbs, Richard A., et al., "Detection of Single DNA Base Differences by Competitive Oligonucleotide Printing," Nucleic Acids Research, vol. 17, No. 7, 1989, pp. 2437-2448.
Tan, Angela Y.C., PhD., et al., "A Simple, Rapid, and Sensitive Method for the Detection of the JAK2 V617F Mutation," American Journal for Clinical Pathology, 2007; 127, pp. 977-981.
Tan, Angela, et al., "Sensitive Detection of KIT D816V in Patients with Mastocytosis," Clinical Chemistry, 52:12, 2006, pp. 2250-2257.
Newton, C.R., et al., "Analysis of any Point Mutation in DNA. The Amplification Refractory Mutation System (ARMS)," Nucleic Acid Research, vol. 17, No. 7, 1989, pp. 2503-2516.
Orou, Andreas, et. al., "Allele-Specific Competitive Blocker PCR: A One-Step Method With Applicability to Pool Screening," Human Mutation 6:163-169, 1995.
Parsons, BL., et al., "ACB-PCR Quantification of K-RAS Codon 12 GAT and GTT Mutant Fraction in Colon Tumor and Non-Tumor Tissue," Cancer Investigation, May 2010; 120(5): pp. 364-375.
Meng, F., et al., "Measurement of Tumor-Associated Mutations in the Nasal Mucosa of Rats Exposed to Varying Doses of Formaldehyde," RegulatoryToxicology Pharmacology., Mar. 31, 2010.

(Continued)

*Primary Examiner* — Young J Kim
(74) *Attorney, Agent, or Firm* — Workman Nydegger

(57) ABSTRACT

Methods are provided for nucleic acid analysis. In an illustrative method, Snapback-ARMS primers are used to amplify preferentially a target nucleic acid that is present in a low allele fraction. In another embodiment, tailed primers are used to identify the preferentially amplified allele.

7 Claims, 22 Drawing Sheets

(56) References Cited

OTHER PUBLICATIONS

Meng, F., et al., "K-RAS Mutant Fraction in A/J Mouse Lung Increases as a Function of Benzo[a]pyrene Dose," Environmental Molecular Mutagenesis, Mar. 2010; 51(2), pp. 146-155.
Verkler, TL, et al., "Populations of P53 Codon 270 CGT to TGT Mutant Cells in SKH-1 Mouse Skin Tumors Induced by Simulated Solar Light," Molecular Carcinogenesis. Nov. 2008; 47(11), pp. 822-834.
Verkler, TL, et al., "Simulated Solar Light-Induced P53 Mutagenesis in SKH-1 Mouse Skin; A Dose-Response Assessment," Molecular. Carcinogenesis, Aug. 2008; 47(8), pp. 599-607.
McKinzie, PB., et al., "ACB-PCR Measurement of K-RAS Codon 12 Mutant Fractions in Livers of Big Blue Rats Treated with N-Hydroxy-2-Acetylaminofluorene," Mutagenesis, Nov. 2006; 21(6), pp. 391-397.
Parsons, BL, et al., "Levels of 4-Aminobiphenyl-Induced Somatic H-Ras Mutation in Mouse Liver DNA Correlate with Potential for Liver Tumor Development," Molecular Carcinogenesis, Apr. 2005; 42(4), pp. 193-201.
Verkler, TL, "Quantifying Levels of P53 Mutation in Mouse Skin Tumors," Environmental Molecular Mutagenesis, Jun. 2005; 45(5), pp. 427-434.
Parsons, BL, "Allele-Specific Competitive Blocker-PCR Detection of Rare Base Substitution," Methods Molecular Biology., 2005; 291, pp. 235-245.
Parsons, PL, et al., "Occurrence of H-Ras Codon 61 CAA to AAA Mutation During Mouse Liver Tumor Progression," Carcinogenesis, Jun. 2002; 23(6), pp. 943-948.
McKinzie, PB, et al., "Detection of Rare K-Ras Codon 12 Mutations Using Allele-Specific Competitive Blocker PCR," Mutation Research., May 27, 2002; 517(1-2), pp. 209-220.
Parsons, BL, et al., "Detection of a Mouse H-Ras Codon 61 Mutation Using a Modified Allele-Specific Competitive Blocker PCR Genotypic Selection Method," Mutagenesis, Nov. 1998, 13(6), pp. 581-588.
Snell, C. et al., "BRCA1 Promoter Methylation in Peripheral Blood DNA of Mutation Negative Familial Breast Cancer Patients with a BRCA1 Tumour Phenotype," Breast Cancer Research, 2008, pp. 1-8.
Li, B., et al., "Genotyping with TaqMAMA," Genomics, vol. 83, 2004, pp. 311-320.
Nielsen, PE, et al., "Sequence-Selective Recognition of DNA by Strand Displacement with a Thymine-Substituted Polyamide," Science 1991; vol. 254, pp. 1497-1450.
Dabritz, J., et al., "Detection of Ki-ras Mutations in Tissue and Plasma Samples of Patients with Pancreatic Cancer using PNA-Mediated PCR Clamping and Hybridisation Probes," British Journal of Cancer, 2005, vol. 92, pp. 405-412.
Dominguez, PL and Kolodney, MS, "Wild-Type Blocking Polymerase Chain Reaction for Detection fo Single Nucleotide Minority Mutations from Clinical Specimens," Oncogene 2005, vol. 24, pp. 6830-6834.
Cha, RS, et al., "Mismatch Amplification Mutation Assay (MAMA): Appilcation to the c-H-ras Gene," PCR Methods and Applications, 1992, vol. 2, pp. 14-20.
Easterday, WR, et al., "Specific Detection of *Bacillus anthracis* using a TaqMan® Mismatch Amplification Mutation Assay," Biotechniques 2005, vol. 38, pp. 731-735.
Whitcombe, D, et al, "Detection of PCR Products using Self-Probing Amplicons and Fluorescence," Nature Biotechnology, vol. 17, pp. 804-807.
Parsons, B L., et al, "Detection of Basepair Substitution Mutation at a Frequency of 1×10-7 by Combing Two Genotypic Selection Methods, MutEx Enrichment and Allele-Specific Competitive Blocker PCR," Environmental and Molecular Mutagenesis, 1998, 32: oo. 200-211.
Li, J., et al, "Replacing PCR with Cold-PCR Enriches Variant DNA Sequences and Redefines the Sensitivity of Genetic Testing," Nature Medicine 2008, vol. 14, No. 5, pp. 579-584.

\* cited by examiner

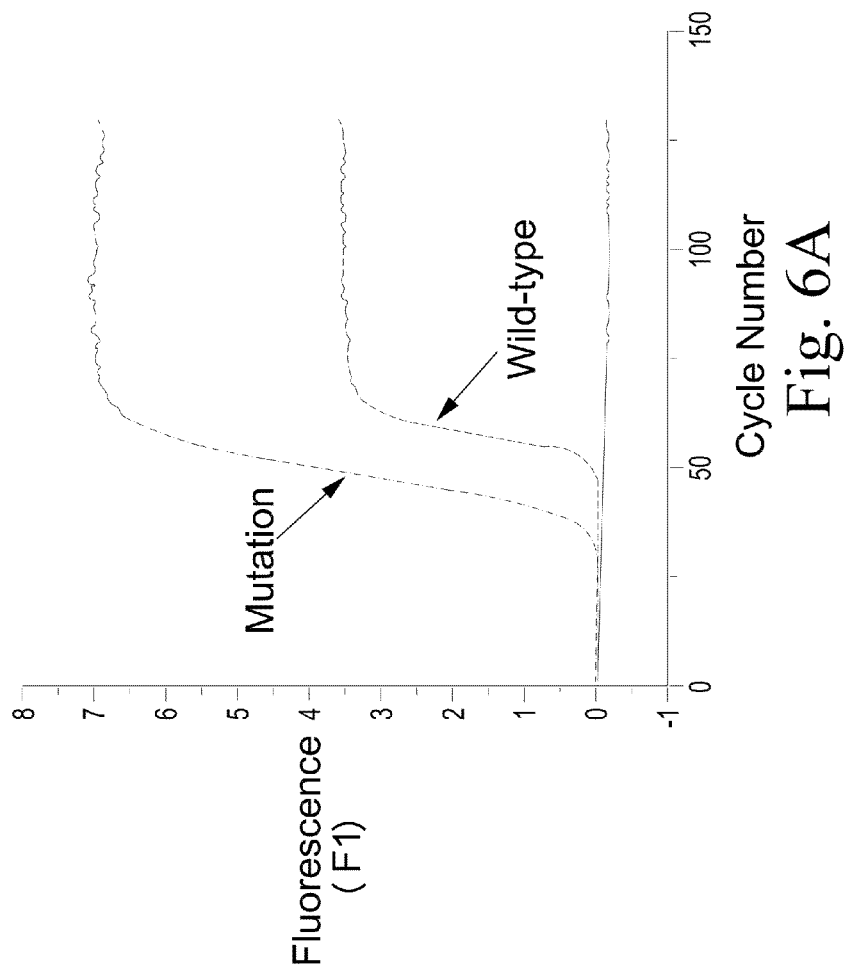

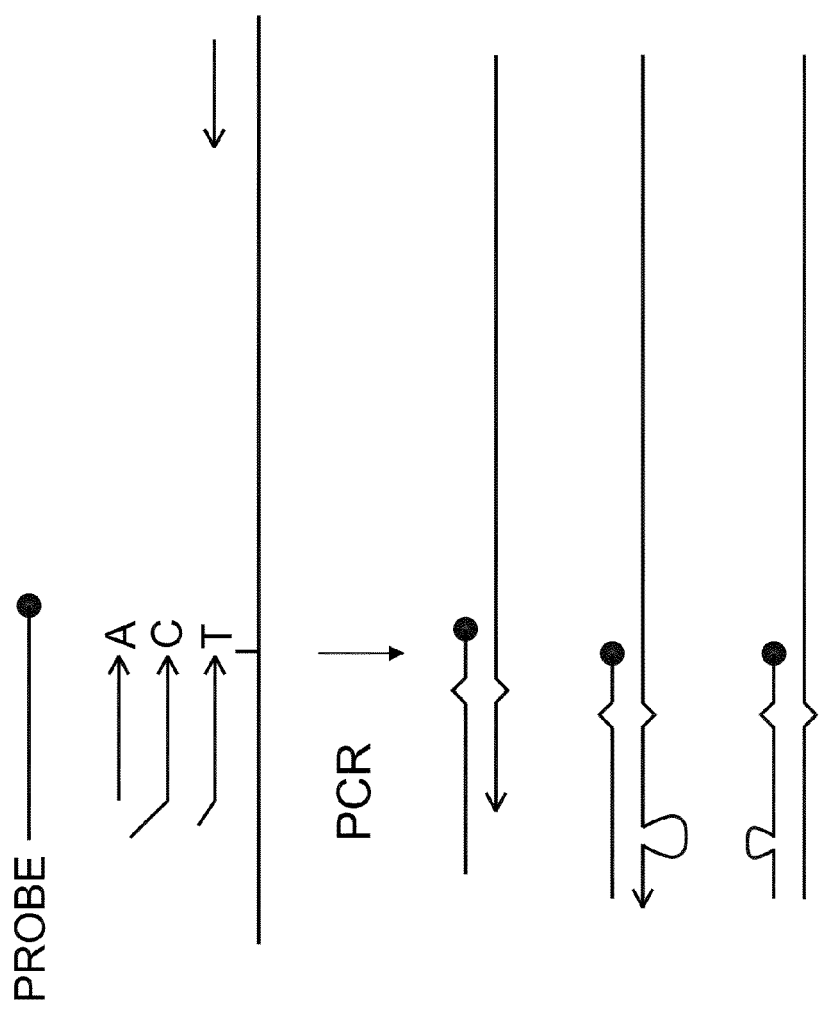

SEQUENCE LISTING

```
<160> NUMBER OF SEQ ID NOS: 21

<210> SEQ ID NO 1
<211> LENGTH: 27
<212> TYPE: DNA
<213> ORGANISM: Homo sapiens

<400> SEQUENCE: 1
tgttttcctt tacttactac acctcag                                27

<210> SEQ ID NO 2
<211> LENGTH: 36
<212> TYPE: DNA
<213> ORGANISM: Homo sapiens
<220> FEATURE:
<221> NAME/KEY: misc_feature
<222> LOCATION: (1)..(2)
<223> OTHER INFORMATION: 5' mismatch
<220> FEATURE:
<221> NAME/KEY: misc_binding
<222> LOCATION: (3)..(15)
<223> OTHER INFORMATION: probe element
<220> FEATURE:
<221> NAME/KEY: misc_binding
<222> LOCATION: (16)..(36)
<223> OTHER INFORMATION: probe element

<400> SEQUENCE: 2
cggctacagt gaaataccca ctccatcgag atttct                      36

<210> SEQ ID NO 3
<211> LENGTH: 22
<212> TYPE: DNA
<213> ORGANISM: Homo sapiens

<400> SEQUENCE: 3
gtgattttgg tctagctaca ga                                     22

<210> SEQ ID NO 4
<211> LENGTH: 24
<212> TYPE: DNA
<213> ORGANISM: Homo sapiens

<400> SEQUENCE: 4
tcagtggaaa aatagcctca attc                                   24

<210> SEQ ID NO 5
<211> LENGTH: 24
<212> TYPE: DNA
<213> ORGANISM: Homo sapiens
<220> FEATURE:
<221> NAME/KEY: mutation
<222> LOCATION: (12)..(12)

<400> SEQUENCE: 5
```
tctagctaca gtgaaatctc gatg                                          24

<210> SEQ ID NO 6
<211> LENGTH: 24
<212> TYPE: DNA
<213> ORGANISM: Homo sapiens
<220> FEATURE:
<221> NAME/KEY: mutation
<222> LOCATION: (9)..(9)
<220> FEATURE:
<221> NAME/KEY: misc_feature
<222> LOCATION: (24)..(24)
<223> OTHER INFORMATION: fluorescein label

<400> SEQUENCE: 6
agctacagtg aaatctcgat ggag                                          24

<210> SEQ ID NO 7
<211> LENGTH: 29
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Red640 label

<400> SEQUENCE: 7
ggtcccatca gtttgaacag ttgtctgga                                     29

<210> SEQ ID NO 8
<211> LENGTH: 28
<212> TYPE: DNA
<213> ORGANISM: Homo sapiens
<220> FEATURE:
<221> NAME/KEY: misc_feature
<222> LOCATION: (1)..(1)
<223> OTHER INFORMATION: FAM label
<220> FEATURE:
<221> NAME/KEY: misc_feature
<222> LOCATION: (28)..(28)
<223> OTHER INFORMATION: BHQ-1 label

<400> SEQUENCE: 8
cggtctagct acagtgaaat ctcgaccg                                      28

<210> SEQ ID NO 9
<211> LENGTH: 17
<212> TYPE: DNA
<213> ORGANISM: Homo sapiens

<400> SEQUENCE: 9
tgtggtagtt ggagcta                                                  17

<210> SEQ ID NO 10
<211> LENGTH: 22
<212> TYPE: DNA
<213> ORGANISM: Homo sapiens
<220> FEATURE:
<221> NAME/KEY: misc_feature
<222> LOCATION: (1)..(7)
<223> OTHER INFORMATION: unique 5' tail

<400> SEQUENCE: 10
ccgcgattgg tagttggagc tc                                            22

<210> SEQ ID NO 11
<211> LENGTH: 21

```
<212> TYPE: DNA
<213> ORGANISM: Homo sapiens
<220> FEATURE:
<221> NAME/KEY: misc_feature
<222> LOCATION: (1)..(4)
<223> OTHER INFORMATION: unique 5' tail

<400> SEQUENCE: 11
ccgctgtggt agttggagct t                                          21

<210> SEQ ID NO 12
<211> LENGTH: 16
<212> TYPE: DNA
<213> ORGANISM: Homo sapiens

<400> SEQUENCE: 12
tggtagttgg agctga                                                16

<210> SEQ ID NO 13
<211> LENGTH: 22
<212> TYPE: DNA
<213> ORGANISM: Homo sapiens
<220> FEATURE:
<221> NAME/KEY: misc_feature
<222> LOCATION: (1)..(7)
<223> OTHER INFORMATION: unique 5' tail

<400> SEQUENCE: 13
ccgcgattgt agttggagct gc                                         22

<210> SEQ ID NO 14
<211> LENGTH: 18
<212> TYPE: DNA
<213> ORGANISM: Homo sapiens

<400> SEQUENCE: 14
tggtagttgg agctggta                                              18

<210> SEQ ID NO 15
<211> LENGTH: 24
<212> TYPE: DNA
<213> ORGANISM: Homo sapiens
<220> FEATURE:
<221> NAME/KEY: misc_feature
<222> LOCATION: (1)..(7)
<223> OTHER INFORMATION: unique 5' tail

<400> SEQUENCE: 15
ccgcgattgt agttggagct ggtc                                       24

<210> SEQ ID NO 16
<211> LENGTH: 24
<212> TYPE: DNA
<213> ORGANISM: Homo sapiens
<220> FEATURE:
<221> NAME/KEY: misc_feature
<222> LOCATION: (1)..(4)
<223> OTHER INFORMATION: unique 5' tail

<400> SEQUENCE: 16
ccgctgtggt agttggagct ggtt                                       24

<210> SEQ ID NO 17
<211> LENGTH: 19
<212> TYPE: DNA
<213> ORGANISM: Homo sapiens
```

```
<400> SEQUENCE: 17
tggtagttgg agctggtga                                              19

<210> SEQ ID NO 18
<211> LENGTH: 25
<212> TYPE: DNA
<213> ORGANISM: Homo sapiens
<220> FEATURE:
<221> NAME/KEY: misc_feature
<222> LOCATION: (1)..(7)
<223> OTHER INFORMATION: unique 5' tail

<400> SEQUENCE: 18
ccgcgattgt agttggagct ggtgc                                       25

<210> SEQ ID NO 19
<211> LENGTH: 25
<212> TYPE: DNA
<213> ORGANISM: Homo sapiens
<220> FEATURE:
<221> NAME/KEY: misc_feature
<222> LOCATION: (1)..(4)
<223> OTHER INFORMATION: unique 5' tail

<400> SEQUENCE: 19
ccgctgtggt agttggagct ggtgt                                       25

<210> SEQ ID NO 20
<211> LENGTH: 22
<212> TYPE: DNA
<213> ORGANISM: Homo sapiens

<400> SEQUENCE: 20
tctctattgt tggatcatat tc                                          22

<210> SEQ ID NO 21
<211> LENGTH: 27
<212> TYPE: DNA
<213> ORGANISM: Homo sapiens
<220> FEATURE:
<221> NAME/KEY: misc_feature
<222> LOCATION: (1)..(5)
<223> OTHER INFORMATION: unique 5' tail

<400> SEQUENCE: 21
ccgcgtgtgg tagttggagc tggtggc                                     27
```

METHODS, COMPOSITIONS, AND KITS FOR RARE ALLELE DETECTION

This application claims priority to U.S. Provisional Application No. 61/245,352, herein incorporated by reference in its entirety.

BACKGROUND OF THE INVENTION

The human genome project has succeeded in sequencing most regions of human DNA. Work to identify the genes and sequence alterations associated with disease continues at a rapid pace. Linkage studies are used to associate phenotype with genetic markers such as simple sequence repeats or single nucleotide polymorphisms (SNPs) to identify candidate genes. Sequence alterations including SNPs, insertions, and deletions that cause missense, frameshift, or splicing mutations then may be used to pinpoint the gene and the spectrum of responsible mutations.

However, even when the genetic details become known, it is difficult to use this knowledge in routine medical practice, in large part because the methods to analyze DNA are expensive and complex. When costs are significantly lowered and the methods dramatically simplified, it is expected that DNA analysis will become accessible for use in everyday clinical practice for effective disease detection and better treatment. Ideal DNA analysis is rapid, simple, and inexpensive.

When a disease is caused by a limited number of mutations, or when a few sequence alterations constitute a large proportion of the disease cases, direct genotyping is feasible. Traditional methods range from classical restriction digestion of PCR products to closed-tube fluorescent methods. Closed-tube methods of DNA analysis can be simple to perform. Once PCR is initiated, no further reagent additions or separations are necessary. However, when one allele is present in small quantities, that allele may be difficult to detect.

Examples of methods that may be used to amplify target oligonucleotide sequences, such as DNA sequences, include the TaqMan assay, a homogenous assay for detecting polynucleotides (see U.S. Pat. No. 5,723,591). In this assay, two PCR primers flank a central probe oligonucleotide. The probe oligonucleotide contains a fluorophore and quencher. During the polymerization step of the PCR process, the 5' nuclease activity of the polymerase cleaves the probe oligonucleotide, physically separating the quencher, which increases fluorescence emission. As more PCR product is created, the intensity of fluorescence emission increases.

Molecular beacons are another method for the detection of polynucleotides (see U.S. Pat. Nos. 6,277,607; 6,150,097; and 6,037,130). Molecular beacons are oligonucleotide hairpins with a fluorophore/quencher pair, and the oligonucleotide undergoes a conformational change when it binds to a perfectly matched template. The conformational change increases the distance between the fluorophore and the quencher, which increases the fluorescence emission from the fluorophore.

Another known method for target sequence detection uses a pair of probes, one of which has an acceptor fluorophore and the other a donor fluorophore, and the probes hybridize to adjacent regions of the target sequence. After amplification of the target sequence, the two probes hybridize with the target sequence and the donor fluorophore interacts with the acceptor fluorophore to generate a detectable signal. The sample is then excited with light at a wavelength absorbed by the donor fluorophore and the fluorescent emission from the fluorescence energy transfer pair is detected for the determination of that target. See U.S. Pat. No. 6,174,670.

U.S. Pat. No. 5,866,336 describes sunrise primers that employ a hairpin structure that is similar to molecular beacons with a fluorescent and quenching moiety, but have a target binding sequence which serves as a primer. During amplification, when the primer's complementary strand is synthesized, the hairpin structure is disrupted, and the quencher is removed from the fluorophore, generating a signal.

Scorpion probes combine a primer with a hairpin structure and contain a sequence that is complimentary to the target sequence. When in the hairpin structure, a quencher moiety is effective in quenching a fluorophore moiety. The hairpin structure is disrupted by the binding of the probe region to the target sequence amplicon attached to the primer, and the quencher moiety is physically removed from the fluorophore, and fluorescent signal can be detected. There are several advantages of such intramolecular reactions over intermolecular probes. Intramolecular hybridization is fast and is not a limiting step, even with the fastest PCR protocols. The probe element is stabilized by the intramolecular reaction, increasing probe melting temperatures by about 5-15° C., so that shorter probes can be used, and in the hairpin or stem-loop format, a single oligonucleotide serves both as one of the primers and as a probe.

These and other methods can be used to detect target sequences, but they all are designed for specific sequences and have expensive detection moieties attached. A method that overcomes some of these issues, particularly for genotyping, is Snapback single strand conformation polymorphism, or "SSCP", which uses a primer of a specific sequence to introduce secondary structure into PCR products that are then separated by electrophoresis. For example, a complementary 8-11 bp primer tail loops back on its complementary sequence in the extension product, creating a hairpin in the single stranded amplicon, which is later detected by gel separation. This method relies on post-amplification gel separation, which is not a technique that can easily transfer to clinical settings, and the additional step increases the time and costs of the assay.

Sequencing is currently the gold standard for identifying sequence variation. Even though costs are decreasing, sequencing is still a complex process that is not rapid, simple, or inexpensive when applied to specific genetic diagnosis or pharmacogenetics. Standard sequencing requires seven steps: 1) amplification by PCR, 2) clean up of the PCR product, 3) addition of cycle sequencing reagents, 4) cycle sequencing for dideoxy termination, 5) clean up of the termination products, 6) separation by electrophoresis, and 7) data analysis. This complexity can be automated and has been in some sequencing centers, but sequencing still remains much more complex than the methods of the present invention. Further, when large or multiple genes are analyzed, often over 90% of the sequenced products come back normal.

Moreover, current sequencing methods fail to identify low copy alleles, particularly when the alleles are present in an allele fraction of less than 20%. Identifying the presence of these low-copy alleles is important in a number of settings, illustratively in identifying the presence of certain oncogene mutations or changes in tumor samples or peripheral fluids such as blood. The presence or absence of such alleles can be particularly important for the selection of treatment protocols, illustratively with detection/confirmation of common somatic mutations (p53, EGFR, BRAF) and early identification of mutant bacterial infections (e.g., malaria) where standard therapies are contraindicated. Other examples of low levels of alleles that can be found against a predominant background are in mitochondrial DNA and fetal DNA present within maternal circulation. In addition, detection of low levels of epigenetic mutations is desired. For example, it was recently found that BRCA1 promoter methylation between 1 and 10% was associated with certain breast cancer phenotypes (Snell et. al., 2008, Breast Cancer Research)

PCR-based techniques for enriching the proportion of minority alleles and mutations in a sample are known. When the genotype of the mutation is unknown, COLD-PCR can be used (Li J, et al., Nat Med 2008; 14:579-84). It is known that this technique can detect down to a 1:100 ratio of mutant allele to wild type. However, because COLD-PCR is nonspecific and detects any variant that occurs, additional analysis is necessary to identify the products. For enriching known SNPs, some of the most popular techniques are ARMS (Newton C R, et al., Nucleic Acids Res 1989; 17:2503-16), PNA-mediated PCR (Nielsen P E, et al., Science 1991; 254:1497-500; Dabritz J, et al., Br J Cancer 2005; 92:405-12), LNA-mediated WTB-PCR (Dominguez P L, Kolodney M S. Wild-type blocking polymerase chain reaction for detection of single nucleotide minority mutations from clinical specimens. Oncogene 2005; 24:6830-4), MAMA-PCR (Cha R S, et al., PCR Methods Appl 1992; 2:14-20), TaqMAMA (Li B, et al., Genomics 2004; 83:31.1-20; Easterday W R, et al., Biotechniques 2005; 38:731-5), and SCORPION® primers (Whitcombe D, et al., Nat Biotechnol 1999; 17:804-7). These methods detect mutations by allele specific PCR, noting differences in quantification cycle (□Cq) and can detect a 1:1000 ratio of mutant allele to wild type.

In ARMS PCR (or PCR amplification of specific alleles (PASA)), one of the primers is designed in such a way that it is able to discriminate among templates that differ by a single nucleotide residue located at the 3'-end of that primer. Only that sequence that matches the 3'-end of the primer is extended efficiently. Thus, an ARMS primer can be designed to amplify a specific member of a multi-allelic system while remaining refractory to amplification of another allele that may offer by as little as a single base from the non-complementary allele.

High resolution melting was introduced as a homogeneous method of scanning PCR amplicons for heterozygous sequence variants. See, e.g., U.S. Pat. Nos. 7,387,887 and 7,582,429, herein incorporated by reference in their entirety. Based on the use of dsDNA saturating dyes, high resolution melting is capable of detecting SNPs and insertions/deletions in amplicons up to 400 bp at a sensitivity >99%. Since its introduction in 2003, additional applications for high resolution melting have been developed, including genotyping for known sequence variants using small amplicons or unlabeled probes (LUNAPROBES™). Unlabeled probes are blocked on the 3'-end to prevent extension during PCR and may use a dsDNA saturation dye, illustratively LCGREEN® Plus (Idaho Technology, Salt Lake City, Utah), to discriminate the genotype of the allele based on probe melting temperature (Tm). The probe sequence can be designed to match either allele and is based on maximizing the ΔTM between the perfect match and mismatched probe. For more information on the use of unlabeled probes, see U.S. Pat. No. 7,387,887, already incorporated by reference.

Snapback primers may also be used for genotyping with or without high resolution melting. With a Snapback primer, the primer comprises a probe element specific for a locus of the target nucleic acid and a template-specific primer region, wherein the probe element is 5' of the template-specific primer region. After amplification, the probe element may hybridize to the locus to form a hairpin in an intramolecular reaction or may hybridize to its complement strand in an intermolecular reaction. Thus, a Snapback primer incorporates the probe element into the same oligonucleotide as the primer. Snapback primers may be labeled, but they are often used unlabeled, in a manner similar to unlabeled probes. See WO 2008/109823, incorporated herein in its entirety, for a detailed discussion of Snapback primers.

It has been found that the probes themselves may be used to bias amplification of low fraction alleles. With minor allele amplification bias (MAAB) techniques, the probe (whether unlabeled probe, Snapback probe element, or other probe) is matched to the higher fraction allele, and "allele amplification bias" is empirically determined by setting the annealing temperature (or extension temperature, if used) of PCR somewhere between the Tm of the perfectly matched and somewhat below the Tm of the mismatched probe. At this mid-Tm annealing temperature, the perfectly matched probe is bound to its target (often the wild type allele) and is stable enough to retard amplification, while the probe melts off of the mismatched allele and extension may proceed unhindered. An exo-polymerase may also be used to avoid probe digestion and aid in biasing amplification of the lower Tm allele. See WO 2010/054254, incorporated herein in its entirety.

SUMMARY OF THE INVENTION

In one aspect of the present invention method for detecting a minor allele in a sample are provided, the methods comprising amplifying DNA comprising the minor allele and a major allele, wherein the minor allele is present in a lower concentration than the major allele, and the minor allele differs from a wild-type allele by a nucleotide, wherein the amplifying step is performed using a pair of primers comprising an ARMS and a second primer, wherein a 3' terminal nucleotide of the ARMS primer matches the nucleotide of the minor allele and is mismatched to the nucleotide of the wild-type allele, and a probe, wherein the probe has a nucleotide that matches the nucleotide of the wild-type allele and is a mismatch to the minor allele, and detecting the minor allele using the probe. In illustrative embodiments the ARMS primer may be a Snapback ARMS primer or the probe may be an unlabeled probe or labeled probe. Illustratively, asymmetric PCR may be used, wherein the ARMS primer is provided at a lower concentration than the second primer.

In another aspect of the invention, methods for detecting one of a plurality of alleles in a sample are provided, the methods comprising amplifying DNA comprising the allele to produce an amplicon, wherein the allele differs from other alleles that may be present in the sample by a nucleotide, wherein the amplifying step is performed using primers comprising a plurality of ARMS primers, wherein each ARMS primer has a 3' terminal nucleotide that matches the nucleotide of one of the alleles and is mismatched to the nucleotide of the other alleles, and each the ARMS primer is provided with a unique 5' tail, melting the amplicon, and identifying the allele using a melting curve from the unique 5' tail. In one illustrative example, the amplifying step also includes a probe that is configured to match the major allele and is mismatched to each of the plurality of alleles, and the identifying step includes using a melting curve generated from melting the probe from the amplicon.

In yet another aspect of the invention, kits for genotyping a minor allele are provided, the kits comprising a pair of primers comprising an ARMS primer and a second primer, wherein a 3' terminal nucleotide of the ARMS primer matches the nucleotide of the minor allele and is mismatched to the nucleotide of the wild-type allele, and a detectable probe, wherein the probe has a nucleotide that matches the nucleotide of the wild-type allele and is a mismatch to the minor allele. The kits may further comprise one or more other components for amplification, such as a polymerase, and dNTPs.

Additional features of the present invention will become apparent to those skilled in the art upon consideration of the following detailed description of preferred embodiments exemplifying the best mode of carrying out the invention as presently perceived.

BRIEF DESCRIPTION OF THE FIGURES

FIG. 4A (0.5 µm), FIG. 4B (0.1 µm), FIG. 4C (0.05 µm).

FIG. 5A is the same as FIG. 4A. In FIGS. 5B-C, the concentration of the reverse primer remains the same, while the concentration of the ARMS primer is reduced as follows: FIG. 5B (0.1 µm), FIG. 5C (0.05 µm).

FIGS. 6A-B is a comparison of symmetric ARMS amplification without a probe (FIG. 6A) and with an unlabeled probe matched to the wild-type allele (FIG. 6B).

FIG. 8A shows the amplification curves, while FIG. 8B shows the melting curves, water (———) B-raf mutation (— — —), wild-type (— — — —), 1/10 B-raf/wt (-·-), 1/10² B-raf/wt (-·-), 1/10³ B-raf/wt (— — — —), 1/10⁴ B-raf/wt (-------) 1/10⁵ B-raf/wt (···· ), 1/10⁶ B-raf/wt (···· ), 1/10⁷ B-raf/wt (———).

FIG. 9A shows the amplification curves, while FIG. 9B shows the melting curves, water (———) B-raf mutation (— — —), wild-type (— — — — — —) 1/10 B-raf/wt (-·-), 1/10² B-raf/wt (-·-), 1/10³ B-raf/wt (— — — —), 1/10⁴ B-raf/wt (-------) 1/10⁵ B-raf/wt (— — — — —), 1/10⁶ B-raf/wt (···· ), 1/10⁷ B-raf/wt (———).

FIG. 10 is a schematic of a method of identifying three different mutant alleles using a probe configured to hybridize to the wild-type allele and three unique 5' tailed primers, each configured to prime amplification of its respective allele and each identifiable by the melting curves due to the tails.

FIG. 11A shows melting curves for K-ras codon 12, position 1, FIG. 11B shows melting curves for K-ras codon 12, position 2, FIG. 11C shows melting curves for K-ras codon 13, position 1, and FIG. 11A shows melting curves for K-ras codon 13, position 2. In each case, the three different mutant alleles are easily distinguishable by the different melting curves of the respective 5' tailed ARMS primers. The identified melting peaks are the melting peaks of the probe, whereas the melting peaks to the right are the full-length amplicons.

DETAILED DESCRIPTION

Figure 1:
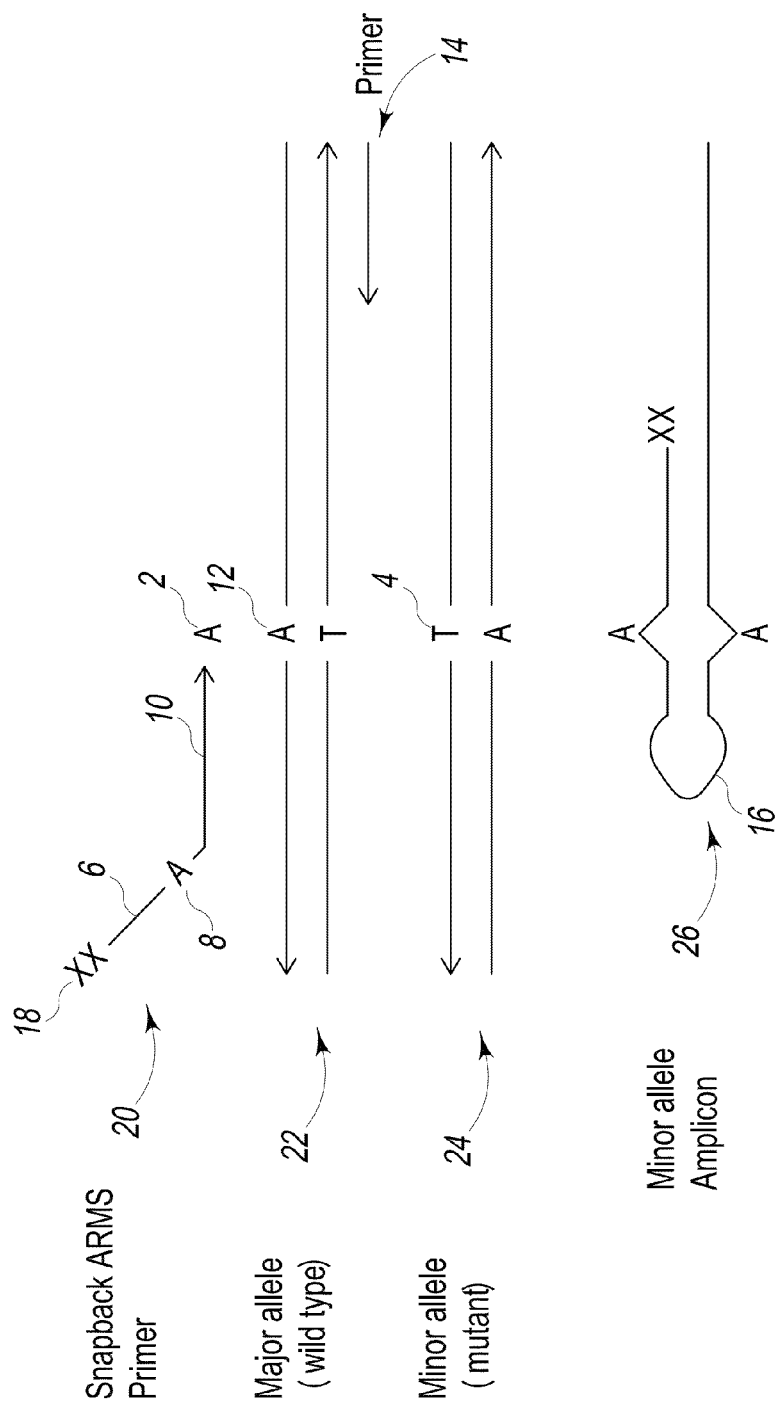
FIG. 1 is a schematic of a Snapback-ARMS primer, used to bias amplification of a minor allele.

In an illustrative embodiment, methods and kits are provided for PCR in which an ARMS primer is combined with a probe designed for biasing amplification. In one illustrative embodiment, the probe is the probe element of a Snapback primer, and thus, one of the PCR primers is a Snapback ARMS primer. In other illustrative embodiments, the probe may be an unlabeled probe or other probe used to bias amplification of the same allele as the ARMS primer. In yet another embodiment, various ARMS primers are provided, each of which is specific for a different allele and each of which is distinctively tailed, allowing for easy identification of amplified allele.

As used herein, the terms "a," "an," and "the" as used herein are defined to mean one or more and include the plural unless the context is inappropriate. Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile) that contains cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thioester linkages). In particular, nucleic acids can include, without limitation, DNA, RNA, cDNA, gDNA, ssDNA, dsDNA or any combination thereof.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes (dyes that fluoresce more strongly when bound to double-stranded DNA than when bound to single-stranded DNA or free in solution) may be used to detect dsDNA.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. (See, for example, F. Ausubel et al., Current Protocols in Molecular Biology, John Wiley & Sons, New York, N.Y., 1998).

Polymerase chain reaction (PCR) is a technique widely used in molecular biology. It derives its name from one of its key components, a DNA polymerase used to amplify a piece of DNA by in vitro enzymatic replication. As PCR progresses, the DNA generated (the amplicon) is itself used as a template for further cycles of replication. This sets in motion a chain reaction in which the DNA template is exponentially amplified. With PCR, it is possible to amplify a single or few copies of a piece of DNA across several orders of magnitude, generating millions or more copies of the DNA piece. PCR employs a thermostable polymerase, dNTPs, and a pair of primers.

While PCR is the amplification method used in the examples herein, it is understood that any amplification method that incorporates a primer may be suitable. Such suitable procedures include polymerase chain reaction (PCR); strand displacement amplification (SDA); nucleic acid sequence-based amplification (NASBA); cascade rolling circle amplification (CRCA), loop mediated isothermal amplification of DNA (LAMP); isothermal and chimeric primer-initiated amplification of nucleic acids (ICAN); target based-helicase dependant amplification (HDA); transcription-mediated amplification (TMA), and the like. Therefore, when the term PCR is used, it should be understood to include other alternative amplification methods that use a primer and can be biased to amplify one allele preferentially.

The disclosed compositions and methods can be used in variations of traditional PCR techniques in order to increase the sensitivity, accuracy, and speed of amplicon detection. Some variations on the basic PCR technique include allele-specific PCR, assembly PCR or polymerase cycling assembly (PCA), asymmetric PCR, helicase-dependent amplification, hot-start PCR, intersequence-specific PCR (ISSR), inverse PCR, ligation-mediated PCR, methylation-specific PCR (MSP), miniprimer PCR, multiplex ligation-dependent probe amplification (MLPA), multiplex-PCR, nested PCR, overlap-extension PCR, quantitative PCR (Q-PCR), RT-PCR, solid phase PCR, TAIL-PCR, touchdown PCR, PAN-AC, and universal fast walking.

While the terms "mutant" (or "mutation") and "wild type" are used herein, it is understood that the minor allele may be other than a mutant allele and the major allele may be other than the wild type. For example, in a sample of maternal blood, the minor allele may be from fetal cells while the major allele may be the maternal allele.

The present invention contemplates use of asymmetric or symmetric PCR assays. Asymmetric PCR can be used to preferentially amplify one strand of the original DNA more than the other. PCR is carried out with an excess of the primers for the chosen strand.

The present invention is directed to methods, compositions, and kits for use in detection of one or more specific DNA sequences, the target sequences, including but not limited to genotyping, and specifically for determining the presence and/or quantity of rare alleles. Genotyping generally refers to detecting specific sequence alterations, e.g. mutation detection. Aspects of the present invention are useful for detecting rare occurrences in DNA, usually mutations, from among a larger population, usually of wild-type DNA sequences. The methods, composition and kits of the present invention can be used for diagnosis, determining treatment regimens, and prognosis.

In one illustrative embodiment, the present invention comprises methods, compositions, and kits that comprise use of Snapback ARMS primers. In other embodiments, detection of target sequences, particularly rare or mutant alleles, may be accomplished by labeled probes, double-stranded nucleic acid detecting dyes, or other methods known in the art for detecting nucleic acid binding of target sequences. Aspects of the present invention comprise single target detection, multiple allele detection, or multiplexed reactions for multiple target detection.

The ability to detect low level mutations from among mostly wild-type DNA would be very useful in areas such as cancer detection, prenatal testing, and infectious diseases. For example, in cancer, low-level (<10%) mutations cannot be sequenced by standard PCR or genotyping techniques. Many moderate- to high-selectivity PCR methods have been developed over the past two decades to enrich minority alleles for known mutations. One of the most widely used approaches is the amplification refractory mutation system (ARMS) which relies on the use of a 3' end terminal nucleotide to enhance the minor allele. The mutation detection sensitivity may range from 1:10 to 1:1000.

ARMS, which is also known as allele-specific PCR (ASP) and PCR amplification of specific alleles (PASA), is a PCR-based method of detecting single base mutations. ARMS has been applied successfully to the analysis of a wide range of polymorphisms, germ-line mutations and somatic mutations. ARMS can discriminate low-levels of the mutant sequence in a high background of wild-type-DNA. ARMS PCR illustratively uses a thermostable polymerase that lacks 3' exonuclease activity. Because the 3' exonuclease activity required for mismatch repair is not present, such polymerases extend primers very inefficiently when the 3' base is mismatched, and the extension of such primers in PCR is a rare event. Thus, by designing primers such that the variable allele is at the 3' nucleotide of one of the primers, one can selectively amplify the matched allele. Traditionally, ARMS generally relies on end-point analysis, such as gel-electrophoresis, for detection.

In the present invention, a probe element is combined with the ARMS primer. In one embodiment, the primer is an ARMS primer with a Snapback probe element, thus creating a Snapback ARMS primer. The ARMS primer portion of the Snapback ARMS primer comprises a terminal 3' nucleotide that is complementary to the minor allele, and thus amplification proceeds from the Snapback ARMS primer, with a 3' terminal nucleotide that is complementary to and primes efficiently from the variable nucleotide of the minor allele. A second primer primes in the opposite direction from a distal location. The second primer may be a standard PCR primer or may be a second Snapback-ARMS primer. The Snapback element of the Snapback ARMS primer is used for detection of the target mutation.

An illustrative aspect of the present invention employs a dsDNA dye and melting analysis to monitor hybridization of a hairpin construct generated from the Snapback ARMS primer, and, thus, detection of the target sequence. According to one aspect of the present invention, after PCR, analysis of the intramolecular melting of the hairpin allows for genotyping of rare or low-copy alleles. Two PCR primers may be used, one a Snapback ARMS primer with a 5'-tail of nucleotides. Optionally, no covalent fluorophores, quenchers, or blockers are needed if double-stranded DNA dyes are used. Thus, in one aspect, the dsDNA dye is not covalently linked to the primer or probe, and is free to bind and be released from the nucleic acid solely based on melting of the double stranded (ds) structure.

In examples shown herein, the wild-type (or major) allele differs from the mutant (or minor) allele by a one base change at the same position in the sequence. As referred to herein, that nucleotide in the wild-type allele is the wild-type nucleotide, and at that same position in the mutant allele is the mutant nucleotide. See FIG. 1 as an illustration, where the wild-type nucleotide is T and the mutant nucleotide is A.

A Snapback ARMS primer comprises a primer configured for amplifying a target nucleic acid, such as in a PCR reaction. A Snapback ARMS primer comprises a probe element specific for a locus of the target nucleic acid. In an illustrative embodiment, a nucleotide that is complementary to the wild-type nucleotide, but mismatched to the mutant or minor allele, is included in the locus in the probe element. As shown, the probe element is completely complementary to the wild-type amplicon but mismatches and is less stable with the mutant allele and post-PCR melting of the probe element can be used for detection of the proper amplicon. With reference to FIG. 1, a Snapback ARMS primer 20 comprises a template-specific primer region 10, and the probe element 6 is 5' of the template-specific primer region 10 of the Snapback ARMS primer. There is a non-binding linking region, illustratively of more than five nucleotides, between the probe element and the primer region, shown as 16 in the amplicon 26. A Snapback ARMS primer 20 may further comprise a 5' mismatch region 18 of from about 1 to about 5 nucleotides, such 5' mismatch region is 5' of the probe region and may function to inhibit PCR extension from the 3' end of the minor strand during the amplification reaction. For more information on the design of Snapback primers, see WO 2008/109823, already incorporated by reference. As discussed above, the Snapback ARMS primer further comprises a 3' terminal nucleotide 2 that will bind to a target sequence minor allele 24 which is to be detected in an amplification reaction, and function as a primer for the amplification reaction of that minor allele. As shown in FIG. 1, the 3' terminal nucleotide 2 is complementary to the mutant nucleotide 4, but is mismatched to the wild-type nucleotide 12 of the major allele 22. As used herein, the 3' terminal nucleotide that binds to a single nucleotide in the target sequence that is usually found as a rare or low number mutant nucleotide is referred to as "the 3' terminal nucleotide". A second primer 14 is also used for amplification.

For example, in a method of the present invention, at least one Snapback ARMS primer is added to an amplification reaction, and amplicons are generated such that the probe element of the Snapback ARMS primer hybridizes intramolecularly to the locus to form a hairpin having a double stranded region. Hairpin amplicons made in reactions primed by a Snapback ARMS primer will have a non-binding nucleotide pair in the double-stranded region of the hairpin. The non-binding site results from the 3' terminal nucleotide of the primer region that is complementary to the wild-type nucleotide of the probe element. See FIG. 1. To detect the mutant allele, a melting curve for the hairpin can be generated by measuring fluorescence from a dsDNA binding dye as the mixture is heated, and the shape and Tm of the melting curve is analyzed.

Combining PCR and Snapback ARMS primers of the present invention for enrichment of minority alleles may comprise use of only two PCR primers. A Snapback ARMS primer may comprise a short-tail 18 of nucleotides at the 5' end that are not complementary to the target sequence (represented as "XX" in FIG. 1), a probe element located 5' to the primer region, wherein the probe element comprises the wild-type nucleotide, a linker region (represented by the darker line in the Snapback ARM primer) and a primer region with a 3' terminal nucleotide that is complementary to a mutant nucleotide. The other primer may be of a standard design, and primes an amplicon from the opposite DNA strand. The hairpin double stranded structure formed by the Snapback ARMS primer may be detected by double stranded binding dyes, and the melting curve of an intramolecular binding event is differentiated from an intermolecular binding event, so that mutant sequences can be detected.

Figure 2:
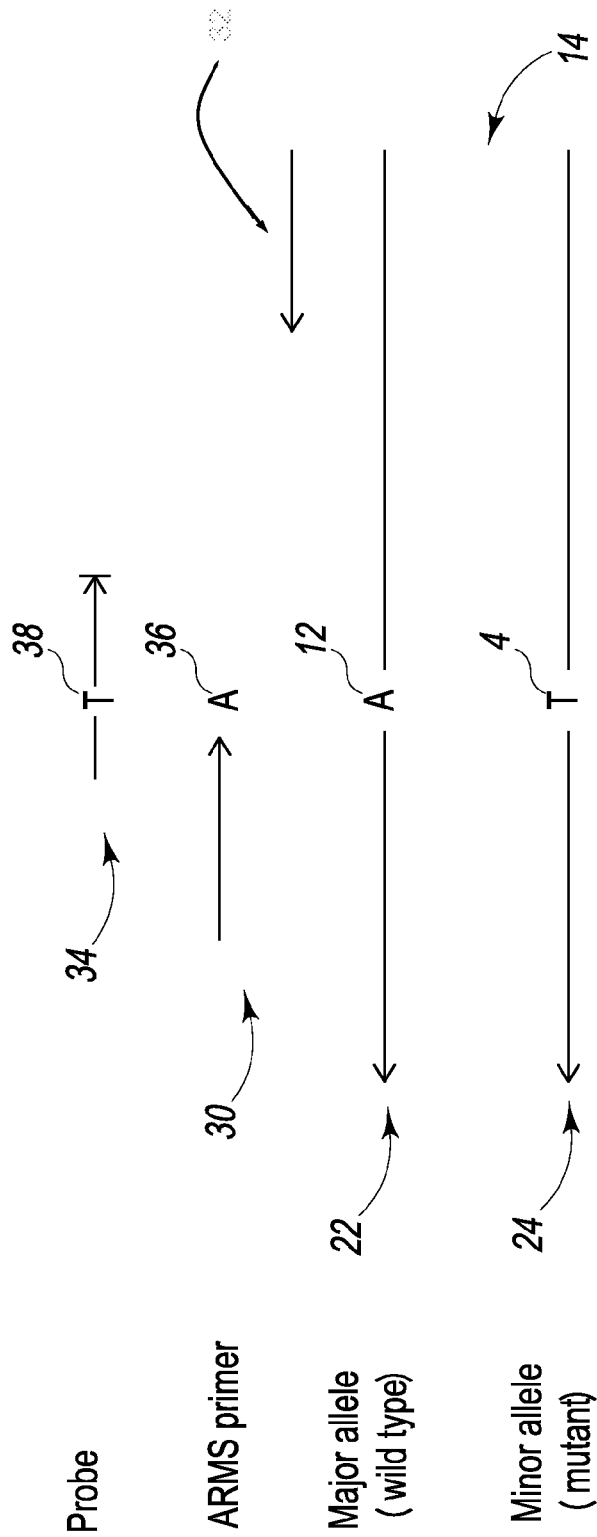
FIG. 2 is a schematic of an ARMS primer and a probe, used to bias amplification of a minor allele.

Another aspect of the present invention is illustrated in FIG. 2 and comprises performing PCR with at least two primers 30, 32 that do not form hairpin structures and one unlabeled probe 34, to improve allele specific PCR. This method is referred to herein as the unlabeled probe ARMS method. At least one of the primers 30 is provided with a 3' terminal nucleotide 36 that is complementary to and binds to the rare or low-copy allele and primes from that site, and is referred to herein as the ARMS primer. At least one other oligonucleotide functions as a probe 34 and its sequence is complementary to the wild-type allele. This probe is blocked on the 3'end to prevent extension. The ARMS primer and the probe are in the same 5' to 3' orientation. The probe is completely complementary to the wild-type allele, and hybridizes to a region that includes the 3' terminal nucleotide of the ARMS primer. Because the probe has a nucleotide 38 that matches the wild-type allele, while the primer has the mismatch, the probe selectively binds to the wild-type allele and blocks amplification of the wild-type allele. The ARMS primer 30, which is completely complementary to the mutant allele 24, binds selectively over the probe 34, and amplification of the mutant allele proceeds. If the ARMS primer 30, instead of the probe 34, should happen to hybridize to the wild-type allele 22, any resulting amplification would be infrequent due to the mismatched 3' terminal nucleotide of the ARMS primer. While it is understood that labeled probes may be used in this embodiment with similar results, by combining an unlabeled probe with an ARMS primer and using dsDNA fluorescent dyes in melting analysis provides an inexpensive detection system.

As a variation of the above embodiment, target sequences can also be detected by labeled probes. Probe based genotyping techniques may use fluorescent labeled probes, such as HybProbes, SimpleProbes, molecular beacons, dual-labeled fluorogenic probes, and Scorpion probes. In such variations, at least one primer is an ARMS primer that selectively extends one allele, while the probe (whether unlabeled probe, labeled probe, or probe element of a Snapback primer or Scorpion primer) binds to another allele more strongly to interfere with amplification of that other allele. Thus, one allele is preferentially amplified by the primer sequence, while amplification of another allele is retarded by the binding of the probe element, which can also be used for detection.

A method for detecting double-stranded DNA comprises use of double stranded dyes or dyes that show a change in fluorescence during PCR reactions. For example, SYBR® Green I (Invitrogen Corp, Carlsbad, Calif.) SYBR® Green I, SYBR® Gold, and ethidium bromide are dyes used for detecting ds DNA and may be used for melting analysis. For example, SYBR® Green I was first used in melting analysis to distinguish different PCR products that differed in Tm (melting temperature) by 2° C. or more, and has been used to identify deletions, genotype dinucleotide repeats, and various sequence alterations. Dyes, such as LCGreen® I and LCGreen® Plus (Idaho Technology, Inc., Salt Lake City, Utah) and other saturation dyes have been developed for high resolution applications, including for genotyping and scanning. When only one PCR product is amplified and the sequence is homozygous, only homoduplexes are formed. With saturation dyes, Tm differences between different homoduplex genotypes are not compressed, and clear differentiation between genotypes is possible, even for SNPs. Such saturation dyes can also be used to identify and distinguish multiple products present in a reaction, such as homoduplexes generated from amplification of multiple loci or multiple targets that are homozygous. When one or more heterozygous targets are amplified, heteroduplex products are readily observable with saturation dyes. The ability to detect and identify heteroduplexes is particularly useful for detecting heterozygous genotypes as well as for scanning unknown mutations.

With saturation dyes, it is possible to distinguish intramolecular binding from intermolecular binding events. Unlabeled oligonucleotides can be used in combination with saturation dyes for genotyping by closed-tube melting analysis. Uses of saturation dyes with unlabeled probes and Snapback ARMS primers are taught in WO 2008/109823 and Zhou, L., et al. Clin. Chem. 2004, each of which is incorporated by reference in its entirety.

Methods using Snapback ARMS primers according to the present invention generally only use two oligonucleotides such as a standard primer and a Snapback ARMS primer. No 3'-end blocking is necessary because a probe element is a part of the 5'-end of the primer, and extension of the primer is desired. Snapback ARMS primer hybridization is intramolecular, and hybridization is rapid and internal structure is less of a concern. When a saturation dye is used, the saturation dye may be present during amplification in sufficient concentration to distinguish the Snapback ARMS primer amplicons hairpins from the wild-type strand amplicons upon amplicon melting. Thus, methods comprising the combination of Snapback ARMS primers and saturation dyes provide closed-tube nucleic acid analysis. While the examples herein use saturation dyes, it is understood that Snapback ARMS primers may be used with other dyes, particularly wherein high resolution is not necessary or where dye addition subsequent to amplification is not an issue. Similar detection methods are available for the unlabeled probe-ARMS embodiments.

In methods of amplification of the present invention, primer ratios may be determined by those skilled in the art, for example, from 10:1, from 2:1 to 20:1, or from 100:1. Unlike with conventional Snapback primers, the Snapback ARMS primer illustratively is the primer provided in the smaller quantity. Probe regions of a Snapback ARMS primer illustratively may comprise between 6 and 28 bases. The Tm of the hairpin duplex can also be adjusted by purposely introducing mismatches, base analogs, or stabilizing moieties into the probe element of the Snapback ARMS primer. For example, bases that result in mismatches to the template can be used to decrease the overall Tm of the hairpin duplex. Mismatches can also be used to mask sequence variants that are best ignored, such as benign polymorphisms. If greater stabilization of the hairpin duplex is desired, locked nucleic acids can be incorporated into the probe element, or a minor groove binder can be attached to increase the melting temperature.

The Snapback ARMS primer forms a hairpin which has a loop structure formed by the ds binding region of the hairpin and includes the linker region, and this loop structure may range in base pair length, illustratively from 17 to 250 base pairs. Other variations on Snapback primers are taught in WO 2008/109823, already incorporated by reference.

EXAMPLES

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

Example 1

Use of Snapback Arms Primer in Arms-Like PCR

Approximately 5% of adult humans have a thyroid nodule. About 5-8% of these thyroid nodules are cancerous. Thyroid fine needle aspiration biopsy (FNAB) with cytological analysis is widely used as an initial diagnostic measure in thyroid nodule evaluation. At least 20% of these biopsies yield an indeterminate cytological finding that cannot distinguish between thyroid cancer and benign tumors. A somatic mutation of the B-raf gene, c.1799 T>A causing a Valine to Glutamate substitution, p.V600E, was cited as the most common change in papillary thyroid carcinoma (PTCs) with more than 80% showing this mutation. There are few methods to detect p.V600E. When HybProbes with standard PCR were used for detecting p.V600E mutation, the sensitivity was about 10%.

Control human genomic DNA and cell line: Wild type human genomic DNA was extracted from human blood. B-raf V600E (c. 1779A) homozygote mutation human cell line HTB-72 was obtained from ATCC (American Type Culture Collection). The genomic DNAs were extracted by using the Puregene DNA-isolation kit (Gentra Systems). DNA concentrations were quantified using a NanoDrop (Thermo Scientific) with absorbance at 260 nm (A260) and adjusted by PCR quantification cycle (Cq). Different mutation to wild type allele fraction ratios were mixed to test the detection sensitivity of a Snapback ARMS primer used in PCR. 500 ng of wild-type c.1799T DNA were used to mix with BRAF homozygous mutation c. 1799A DNA to make ratios of mutation to wild type of 1:1, 1:2, 1:4, 1:8, 1:16, 1:32, 1:64, 1:128, 1:256, 1:512, 1:1024. 1:2048, 1:4096, 1:8192, 1:16384, 1:32, 768 and 1:65,536 (with 200 ng of wild-type human genomic DNA in each reaction). Twelve synthetic K-ras mutation DNA were used for the test.

Clinical samples: Samples were obtained from a total of 47 patients. 44 of these samples had both tumor tissue and fine needle aspiration (FNA) thyroid nodule specimens while the remaining 3 patients had only FNA samples. All samples were provided by ARUP Laboratories and were pretested using a HybProbes assay.

Primers: For snapback-ARMS primer PCR assays, forward primer (5'-tgttttcctttacttactacacctcag (Seq. ID No. 1)) and reverse primer (5'-cgGCTACAGTGAAAT ACCCACTC-CATCGAGATTTCT (Seq. ID No. 2)) were used to amplify an 111 bp product. The reverse primer is the Snapback ARMS primer, with the 3' terminal nucleotide complementary to the mutation, the underlined sequence being the probe element, and the lower-case base pairs being mismatched with the template to prevent extension when in the hairpin configuration.

PCR and melting conditions: PCR was performed in 10 µl reaction volumes containing 2 mmol/L MgCl2, 50 mmol/L Tris (pH 8.3), 500 mg/L bovine serum albumin, 200 µmol/L of each deoxynucleotide triphosphate, 0.4 units KlenTaq polymerase (AB Peptides), 64 ng/µl Anti-Taq Monoclonal antibody (eENYME), 0.5× LCGreen Plus (Idaho Technology), 0.05 µg forward primer, 0.5 µg snapback ARMS primer (reverse), and 200 ng human genomic DNA. PCR was performed in a LightCycler (Roche). The PCR protocol for B-raf with a Snapback ARMS primer was as follows: denature at 95° C. for 2 minutes followed by 70 cycles of 95° C. (0 s hold) and 64° C. (4 s hold). Following PCR, a DNA melting protocol from 55° C. to 92° C. with a 0.2° C./s ramp rate was used.

In this example, the Snapback ARMS primer loop size is smaller than the primer, which reduces the synthesized length. The use of smaller snapback loops also provides a higher Tm than a standard probe element, with a probe melting peak between 60° C. to 68° C. respectively (Newton C R, Graham A, Heptinstall L E, Powell S J, Summers C, Kalsheker N, et al. Analysis of any point mutation in DNA. The amplification refractory mutation system (ARMS). Nucleic Acids Res 1989; 17:2503-16). A 13 bp probe element was used to detect the B-raf mutation. The 3' end of the primer hybridizes to the mutation A (mutant nucleotide), thus selectively amplifying the mutant allele. The probe element includes the wild type nucleotide (T in FIG. 1) and hybridizes to the allele and amplification of wild type is inhibited. The wild type amplification was blocked essentially completely, and high resolution melting is not necessary.

Figure 3:
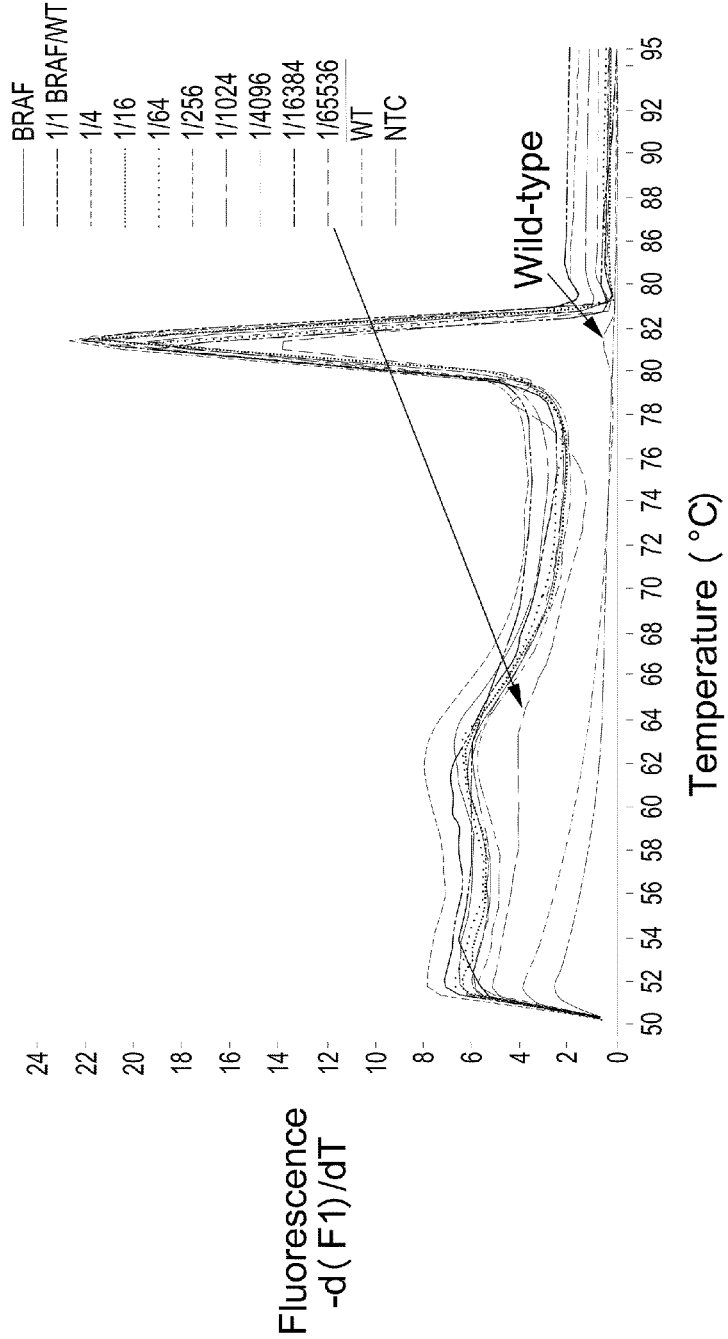
FIG. 3 shows melting peaks for B-raf V600E and wild type serial dilutions used for the rare allele detection sensitivity using. Snapback-ARMS primers: B-raf (———) 1/1 B-raf/wt, 1/4 B-raf/wt (-------) 1/16 B-raf/wt (··········) 1/64 B-raf/wt (··········), 1/256 B-raf/wt (-·-), 1/1024 B-raf/wt (— · —), 1/4096 B-raf/wt (-·-), 1/16,384 B-raf/wt, 1/65,536 B-raf/wt (— — — —), wt (-·-), and no template control (— — — — —). A probe melting peak is identifiable for the 1/65,536 dilution, while there is only a small melting peak for the 100% wild-type sample.

Sensitivity of Snapback-ARMS: The B-raf V600E and wild type serial dilutions above were used for the rare allele detection sensitivity study of Snapback-ARMS primers. The 1:655,536 mutation vs. wild type ratio was detected (FIG. 3), with only one mutation copy present in the 1:655,536 mixture. In another experiment, PCR was run with 4 µg of wild type DNA and 40 mutation copies in a 384 well plate on an LC480 (Roche), and mutations in 38 of the samples were detected. This suggests that a single copy mutation is detectable using the disclosed snapback method.

Blinded study: Snapback ARMS primer detection methods of the present invention were used with tissue samples obtained from 47 patients, with an additional 44 samples that were previously tested to be negative. A blinded test was conducted with Snapback ARMS primers as disclosed herein. All positives were detected with the Snapback ARMS primers, and an additional four more B-raf V600E positives were also found using the Snapback ARMS primers of the present invention than were reported in the 44 deemed-negative samples. All the other samples corresponded to the original diagnosis (data not shown).

Example 2

Use of Unlabeled Probe-Arms Primers and Labeled Probe-Arms Primers in PCR

Forward primer 5'-GTGATTTTGGTCTAGCTACAGA (Seq. ID No. 3) (ARMS primer) and reverse primer 5'-TCAGTGGAAAAATAGCCTCAATTC (Seq. ID No. 4)

were used for ARMS amplification without probe and ARMS combined with probe (unlabeled probe, HybProbe and molecular beacon probe). The 3' end of the forward primer is a perfect match to the BRAF mutation p.V600E (c.1799 T>A). The sequence of the unlabeled probe is 5'-TCTAGCTACAGTGAAATCTCGATG-P (Seq. ID No. 5)

The sequences of the HybProbes are

5'-AGCTACAGTGAAATCTCGATGGAG-Fluorescein (Seq. ID No. 6) and

Red640-GGTCCCATCAGTTTGAACAGT-TGTCTGGA-P (Seq. ID No. 7).

The sequence of the molecular beacon is

5'-FAM-CGGTCTAGCTACAGTGAAATCTCGACCG-BHQ1 (Seq. ID No. 8).

The underscored nucleotide in each of these probe systems is the perfect match for the wild-type allele at the site of the mutation.

PCR was performed in 10 µl reaction volumes containing 2 mmol/L MgCl2, 50 mmol/L Tris (pH 8.3), 500 mg/L bovine serum albumin, 200 µmol/L of each deoxynucleotide triphosphate, 0.4 units KlenTaq polymerase (AB Peptides), 64 ng/µl Anti-Taq Monoclonal antibody (eENZYME), 0.5× LCGreen Plus (Idaho Technology), >500 ng human genomic DNA.

For symmetric PCR, both forward and reverse primer concentrations were 0.5 µM unless otherwise indicated. For 5-fold asymmetric PCR, the ARMS primer was 0.1 µM and the reverse primer was 0.5 µM. For 10-fold asymmetric PCR, the ARMS primer was 0.05 µM and the reverse primer was 0.5 µM. Ten-fold asymmetric PCR provided higher specificity and so was used for ARMS combined with probe (unlabeled probe, HybProbe or molecular beacon probe) with the probe concentration at 0.5 µM. While 10-fold asymmetric PCR is used herein, it is understood that this is exemplary only, and that other asymmetric PCR may be used, illustratively 2-fold, 5-fold, or more than 10-fold, with the ARMS primer provided in the lessor amount.

PCR was performed with a LightCycler 1.2 (Roche). The PCR protocol for unlabeled probe-ARMS, HybProbe-ARMS, molecular beacon-ARMS. and snapback-ARMS was to denature at 95° C. for 1 minute followed by 70 cycles of 95° C. (0 s hold) and 64° C. (4 s hold). Following the PCR, the melting for unlabeled probe-ARMS and snapback-ARMS was to denature at 55° C. to 92° C. with a 0.2° C./s ramp rate. The PCR melting protocol for HybProbe-ARMS and molecular beacon-ARMS was to hold at 50° C. for 1 minute and then perform DNA melting from 50° C. to 75° C. with a 0.1° C./s ramp rate.

According to a previous study (Ayyadevara S, Thaden J J, Shmookler Reis R J. Discrimination of primer 3'-nucleotide mismatch by taq DNA polymerase during polymerase chain reaction. Anal Biochem 2000; 284:11-8), because of the mismatch to wild-type at the 3' end of the ARMS primer, the ARMS primer will amplify the mutant allele while minimizing amplification of the wild-type. BRAF mutation p.V600E is c.1799 T>A. The forward primer with a 3'end A selectively amplifies the mutation c.1799A and the wild type amplification will be minimized due to the A::A mismatch at the 3' end, which suppresses the wild-type better than a T::T mismatch (FIG. 1).

Figure 4A:
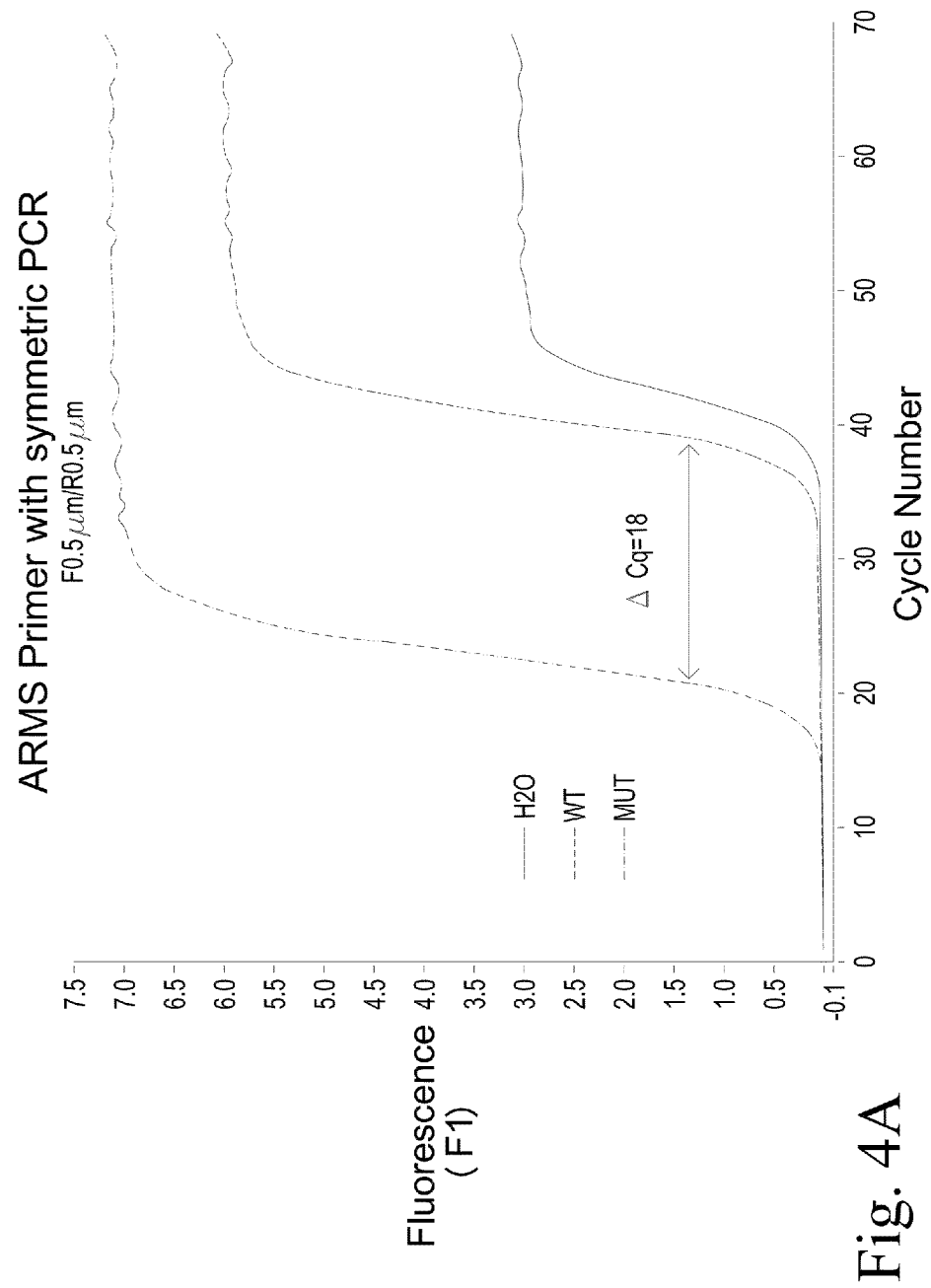
FIGS. 4A-C shows symmetric amplification using ARMS primers, wherein the primer concentration for both primers is.
Figure 4B:
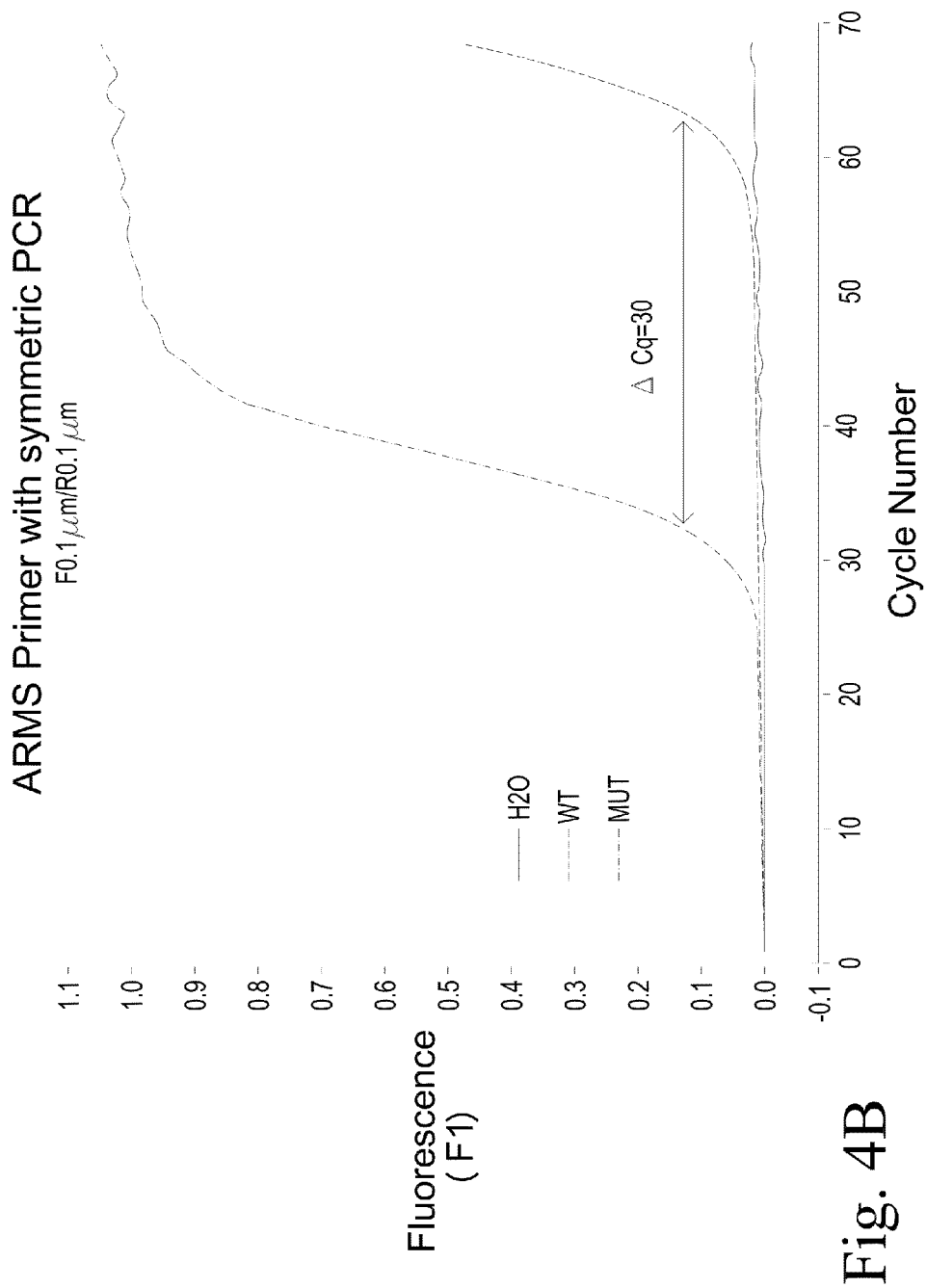
Figure 4C:
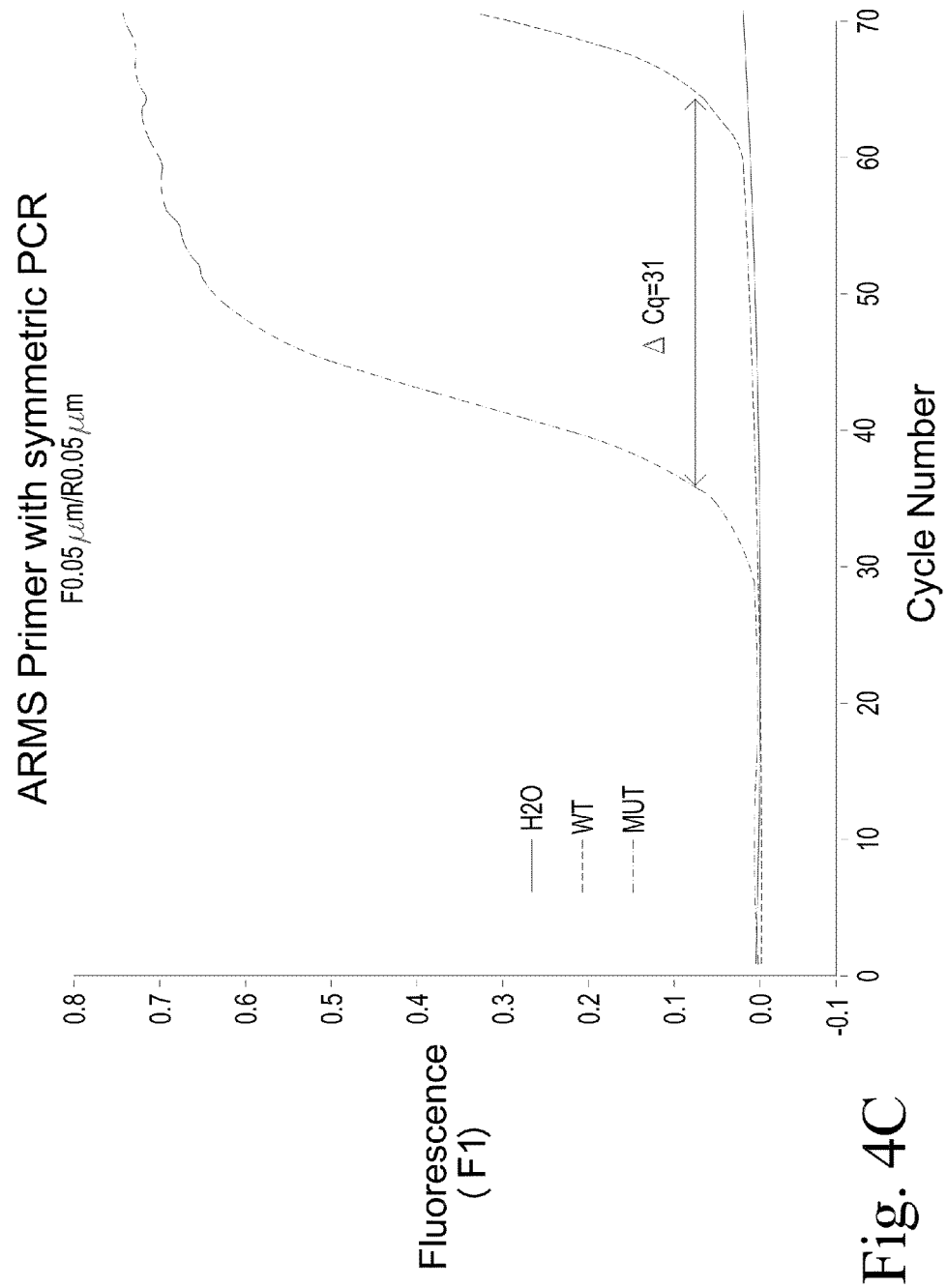
Figure 5A:
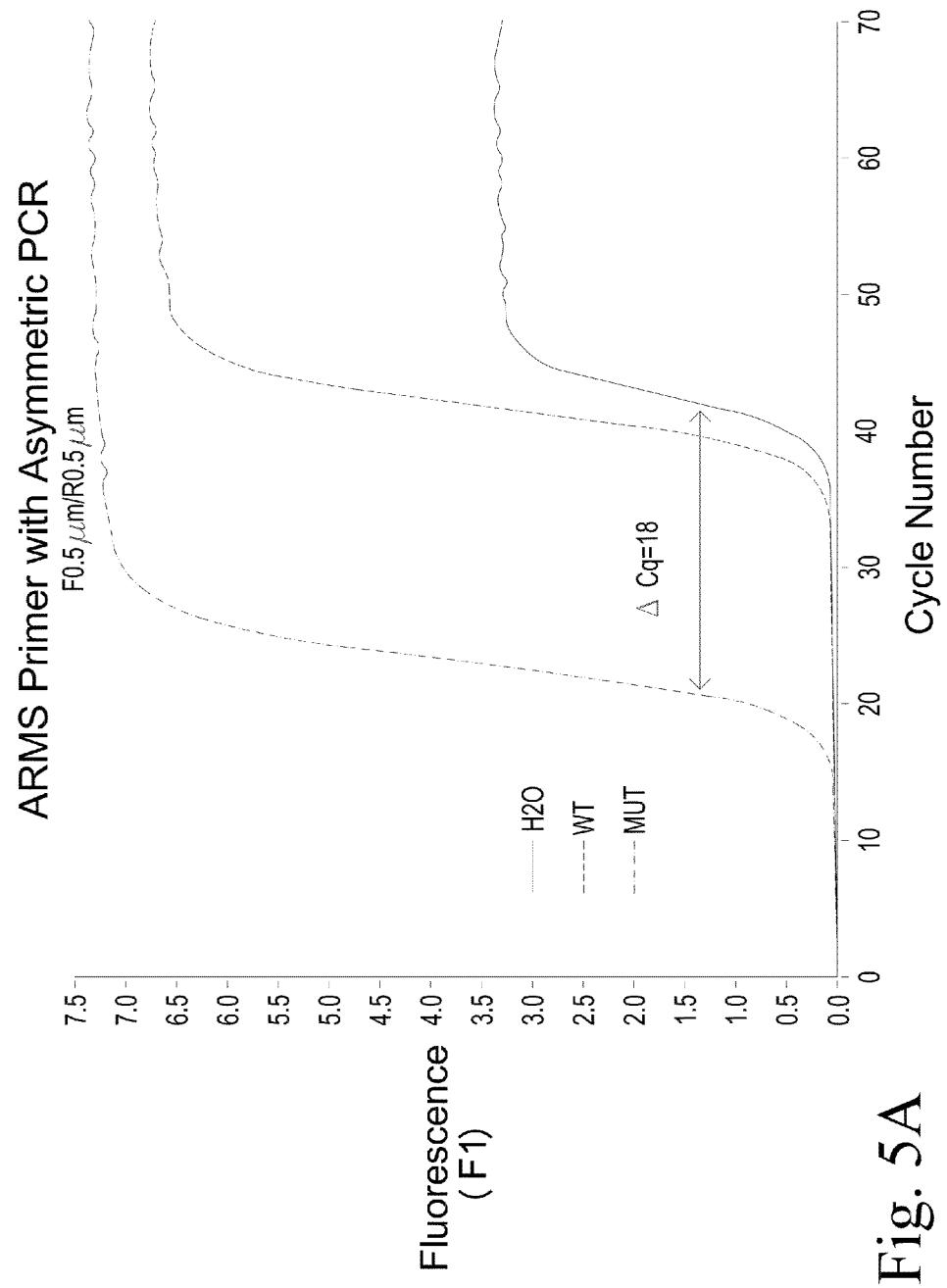
FIGS. 5A-C shows asymmetric amplification using ARMS primers.
Figure 5B:
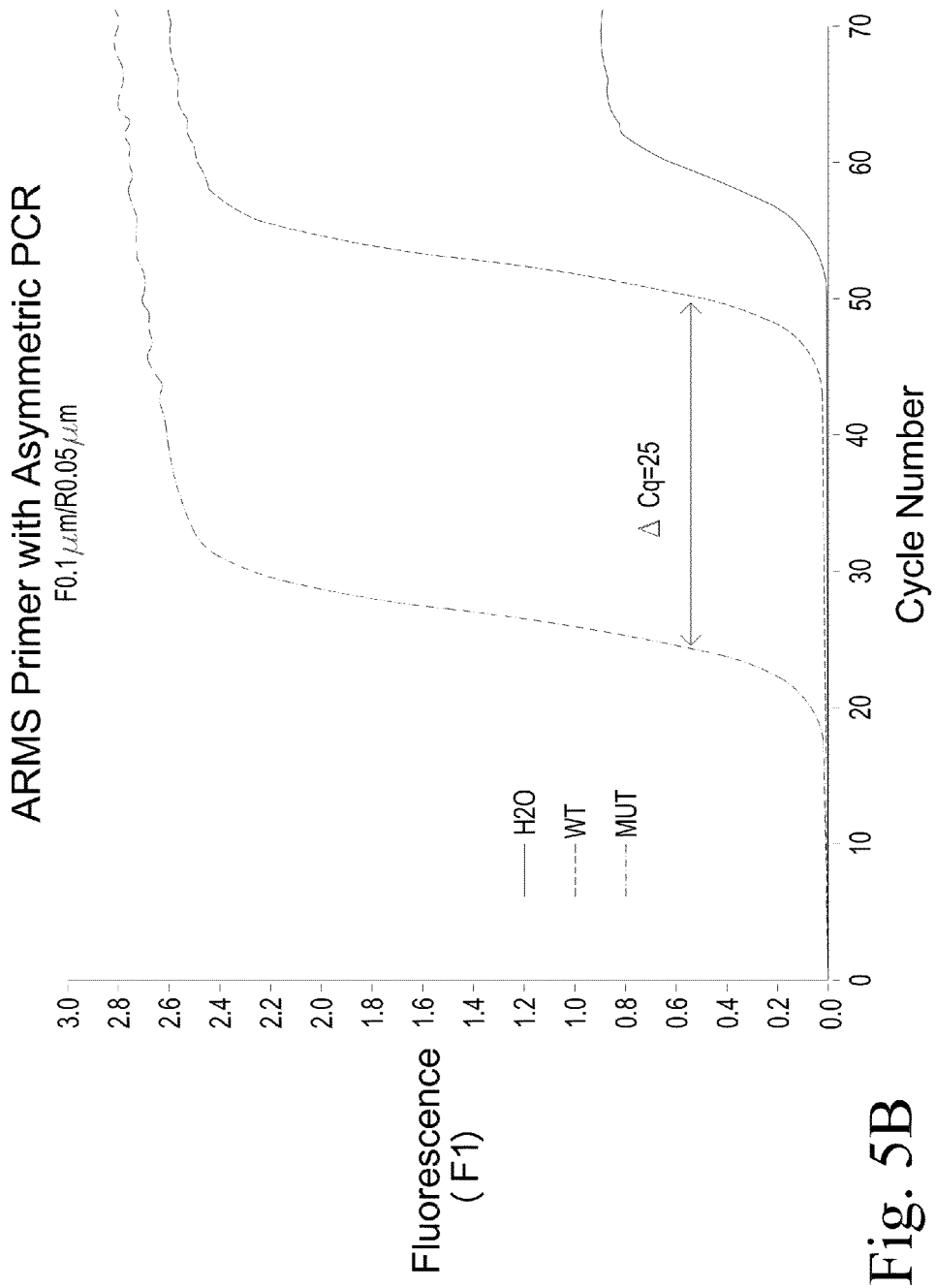
Figure 5C:
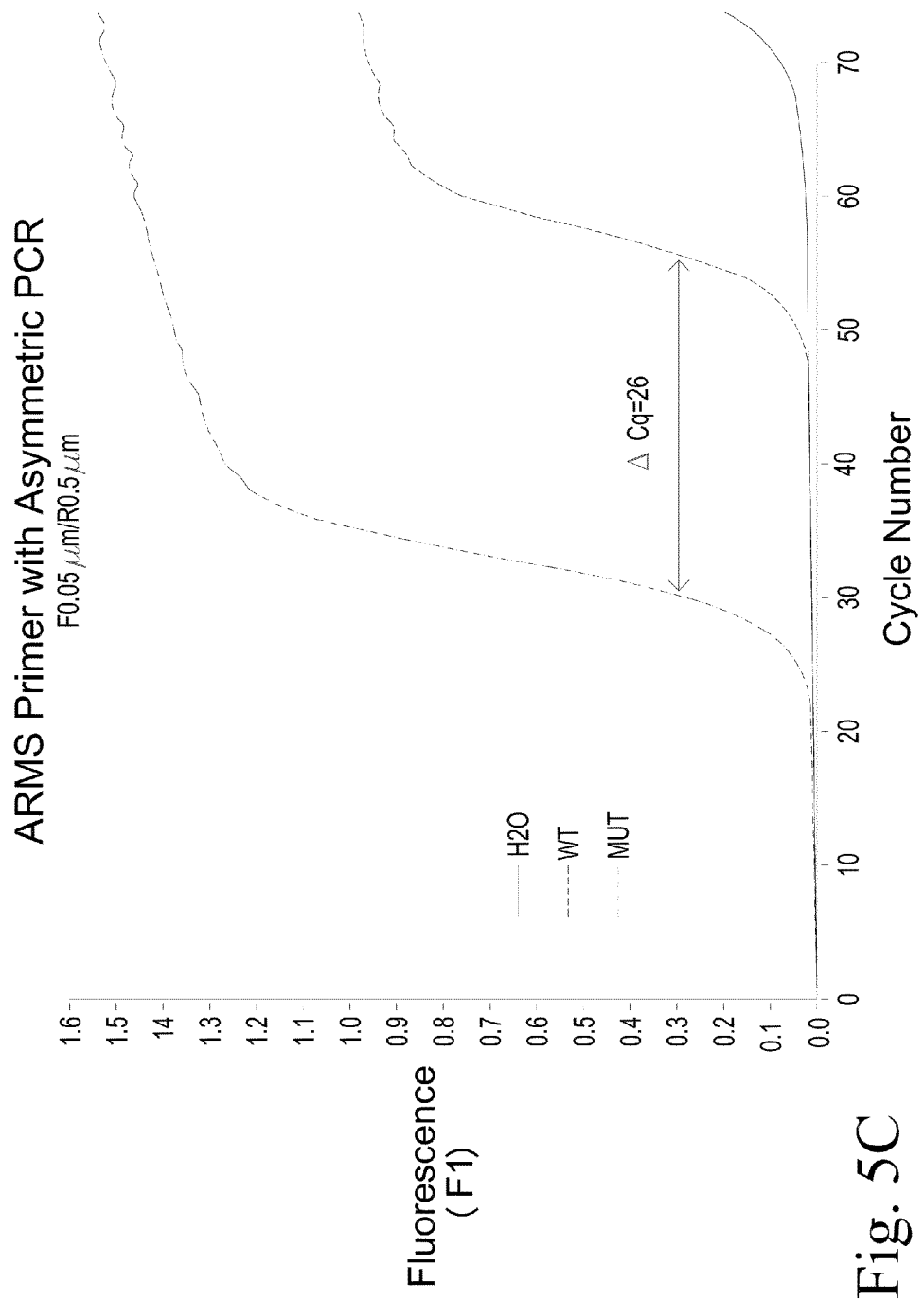

It has been found that the ARMS primer concentration affects the sensitivity of minor allele detection. Lower concentrations of ARMS primers will increase the sensitivity of minor allele detection. Without being bound to theory, it is believed that this is because the ARMS primer is less efficient at annealing to the wild-type allele if it is present at the lower the primer concentrations. At the higher concentrations, there is some priming of the wild-type allele, even with the 3' mismatch. FIGS. 4A-C show the difference of quantification cycle ($\Delta$Cq) for symmetric PCR between BRAF mutation p.V600E and wild-type with different primers concentration. As seen in FIG. 4A, with both forward and reverse primer concentrations at 0.5 µM, the $\Delta$Cq between BRAF mutation and wild-type is 18 cycles. As both primers decrease to 0.1 µM (FIG. 4B) and 0.05 µM (FIG. 4C), the $\Delta$Cq increases to 30 and 31 cycles respectively, indicating the mutation detection sensitivity increased about 4000 ($2^{12}$) and 8000 ($2^{13}$) fold. FIGS. 5A-C show the difference of quantification cycle ($\Delta$Cq) for asymmetric PCR between BRAF mutation p.V600E and wild-type. Compared with 0.5 µM symmetric PCR ($\Delta$Cq=18), decreasing the ARMS primer (forward primer) to 0.1 µM (FIG. 5B) and 0.05 µM (FIG. 5C), the $\Delta$Cq increased to 25 and 26 cycles respectively, indicating the mutation detection sensitivity increased about 120 ($2^7$) and 250 ($2^8$) fold.

With symmetric and asymmetric PCR, when decreasing both primers, the mutation detection sensitivity is higher ($\Delta$Cq=31 with 0.05 µM symmetric PCR, $\Delta$Cq=26 with 0.05 µm forward and 0.5 µm reverse). However, the PCR efficiency of asymmetric PCR is lower (about 10 cycles later). Furthermore, 10× asymmetric PCR is useful for probe detection by increasing the probe signal.

By combining ARMS and probe based genotyping techniques, one can enhance minor allele discrimination. In this example, unlabeled probe-ARMS is used to demonstrate the principle of the probe-ARMS minor allele enrichment technique. Probe-ARMS PCR double-suppressed the wild-type because of the following: 1) the ARMS primer was designed to selectively amplify the mutation but not wild-type, and 2) the unlabeled probe (3' end blocked oligonucleotides) was designed to form a perfect match with the wild-type allele (mismatched to other alleles). Therefore, the probe blocks the primer from annealing to the wild-type template, while simultaneously permitting the primer to anneal to, and amplify the mutant template. Wild-type amplification is essentially completely blocked, and the mutation is enriched.

Figure 6B:
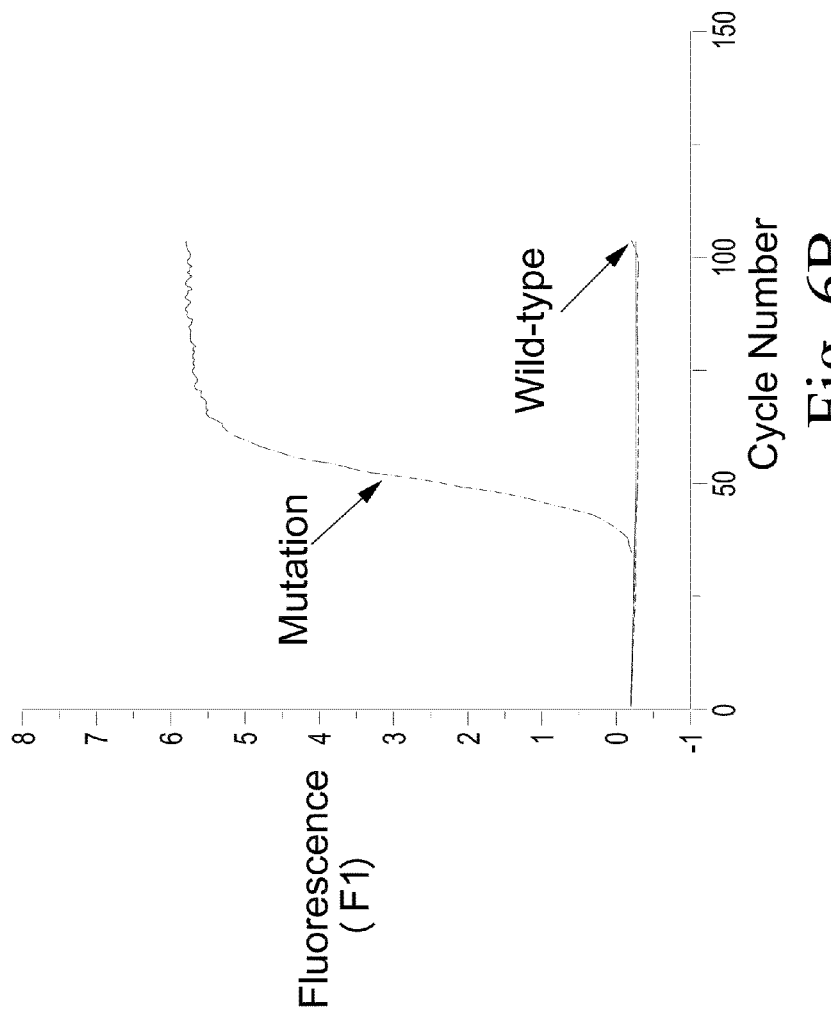
Figure 7A:
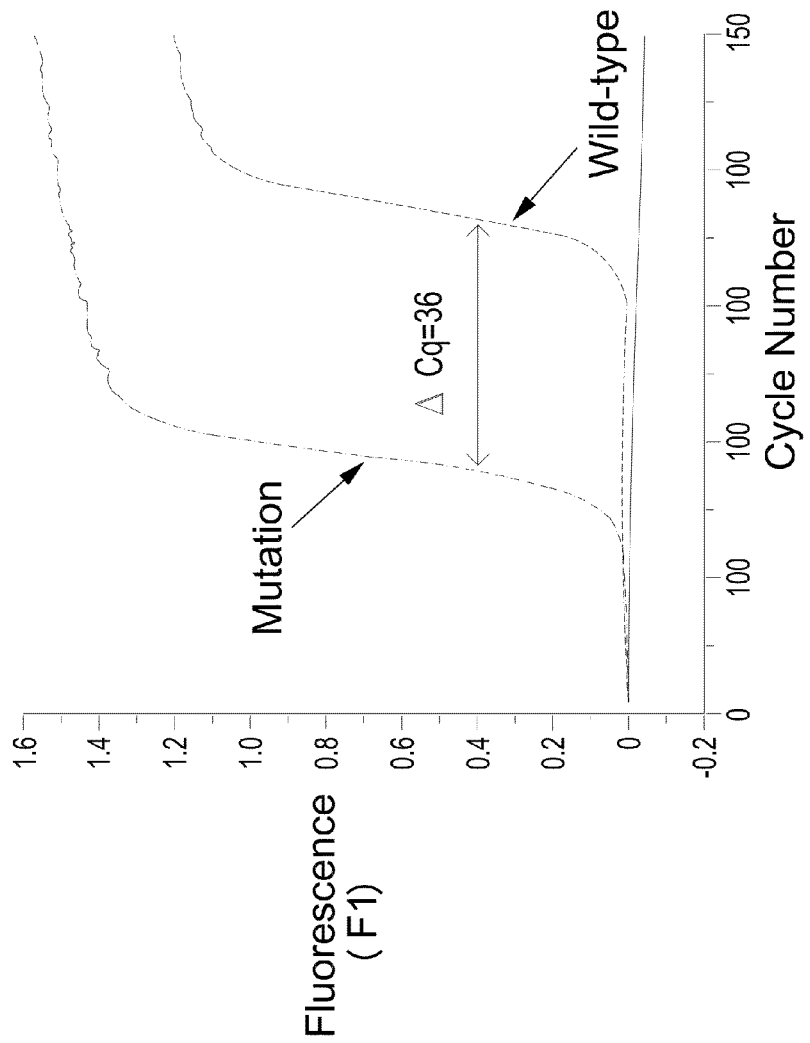
FIGS. 7A-B is a comparison of asymmetric ARMS amplification without a probe (FIG. 7A) and with an unlabeled probe matched to the wild-type allele (FIG. 7B).
Figure 7B:
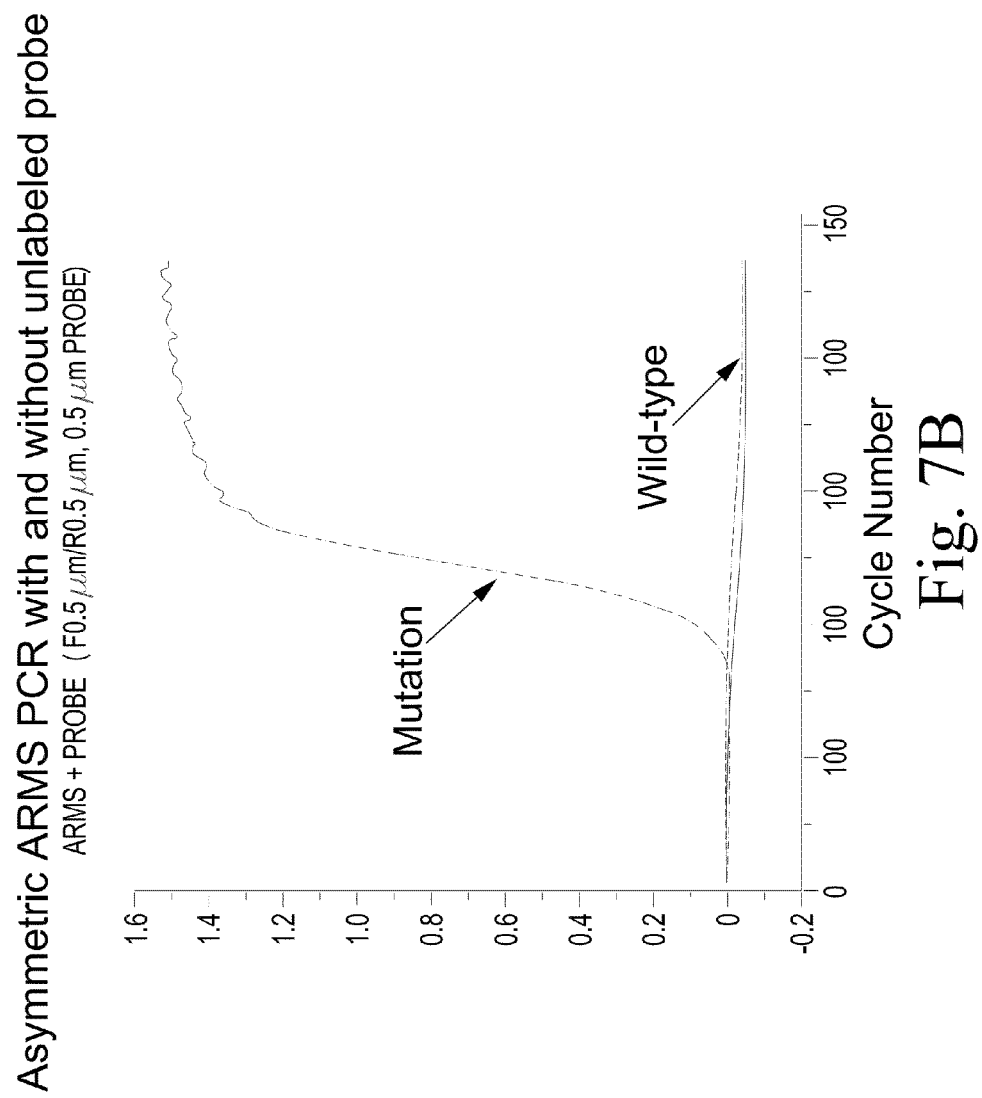

The unlabeled probe blocks wild-type amplification in symmetric PCR and asymmetric PCR. It has been found that with 0.5 µM symmetric PCR with only the ARMS primer that this will selectively amplify the mutation but also amplifies the wild-type with approximately 20 additional cycles (FIG. 6A). If amplification is carried out for enough cycles, this potentially results in false positives. For ARMS primer plus unlabeled probe with 0.5 µM symmetric PCR, the wild-type was suppressed by the unlabeled probe during the amplification, with no measurable amplification after 100 cycles (FIG. 6B). In combining asymmetric ARMS PCR with the use of an unlabeled probe matched for the wild-type. FIGS. 7A-B show 10-fold asymmetric PCR ARMS compared with ARMS plus unlabeled probe (0.05 µM forward, 0.5 µM reverse, 0.5 µM unlabeled probe). For PCR with ARMS only, both mutation and wild-type were amplified, although the wild-type came up about 15 cycles later than the mutation (FIG. 7A). For PCR with ARMS plus unlabeled probe, the wild-type was suppressed essentially completely (FIG. 7B).

As discussed above, the unlabeled probe was designed as a perfect match to the wild-type and the probe Tm for wild-type is 67° C. and 62° C. for the mutation. At 64° C. temperature, the probe will bond on the wild-type allele but not the mutation, with the Taq polymerase still functioning efficiently. Therefore, 64° C. was chosen as the annealing and extension temperature, providing maximum amplification suppression of the wild-type allele. Illustratively, an annealing temperature is chosen that is between the annealing temperature of the probe to wild-type and of the probe to mutant. However, it is understood that any annealing temperature is sufficient that allows for the probe to bind to the wild-type allele while allowing extension of the minor allele. For more information on selection of appropriate annealing temperatures to bias amplification away from the allele matched to the probe, see WO 2010/054254, already incorporated by reference.

Figure 8A:
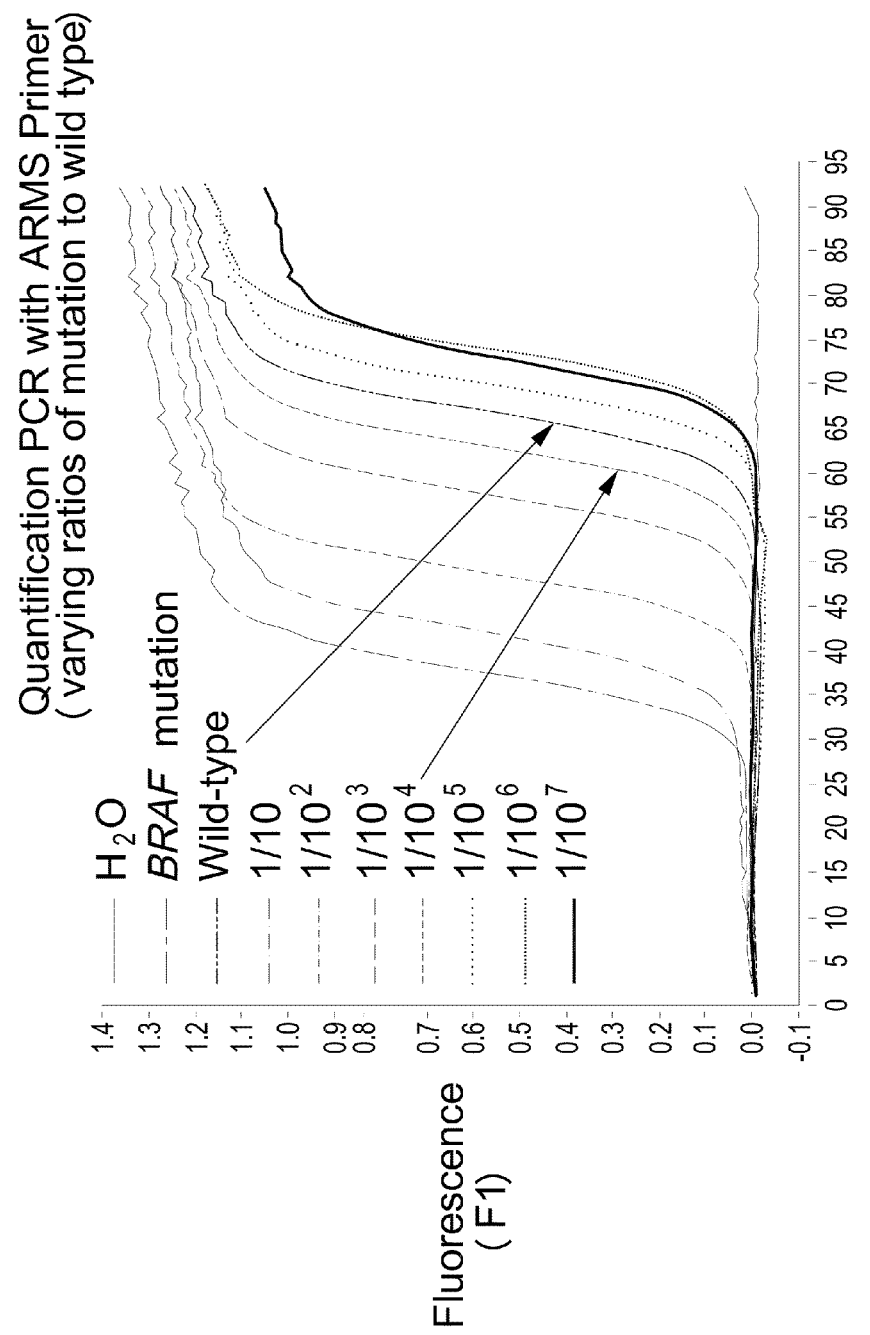
FIGS. 8A-B show the comparison of 10-fold ARMS asymmetric PCR without an unlabeled probe.
Figure 8B:
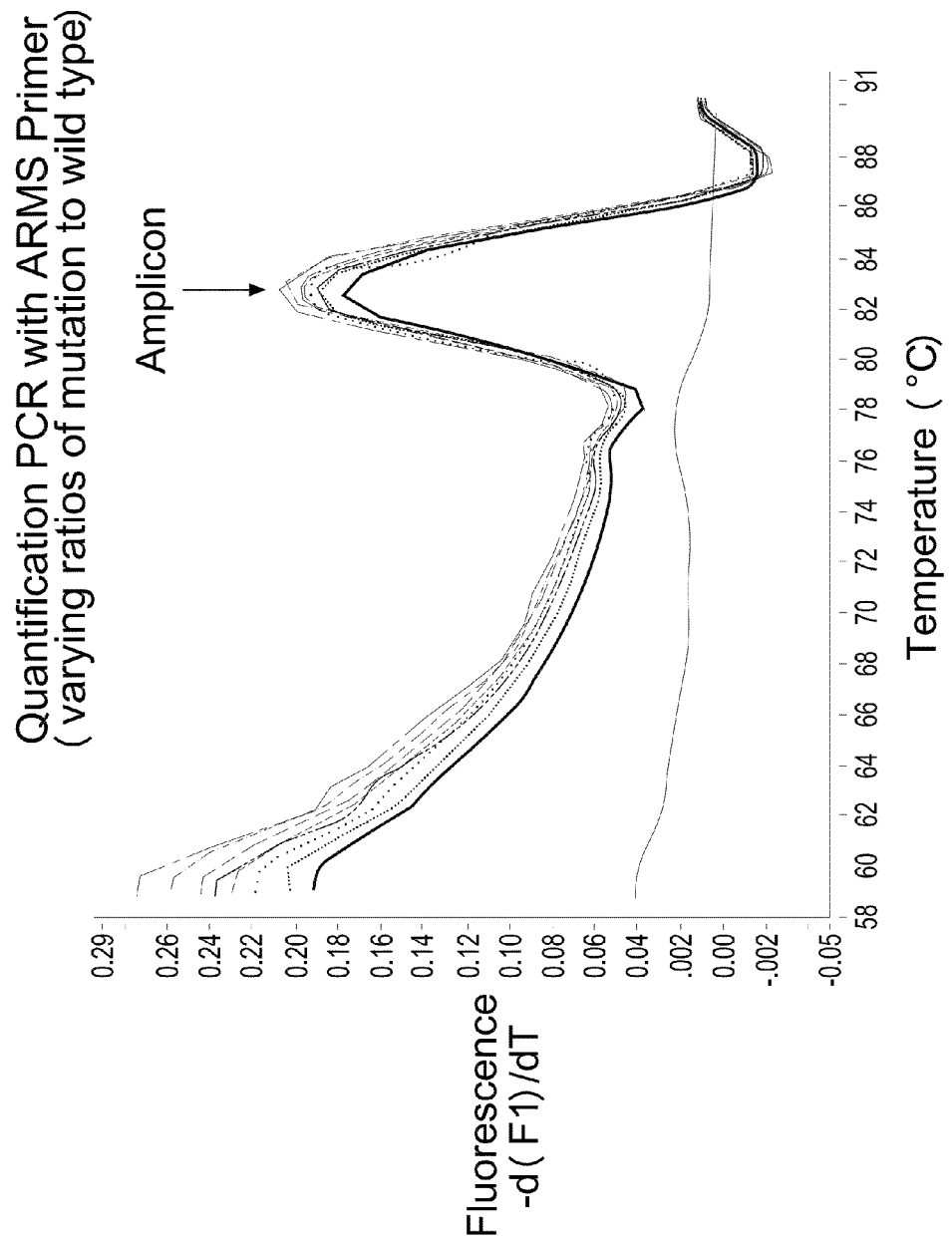
Figure 9A:
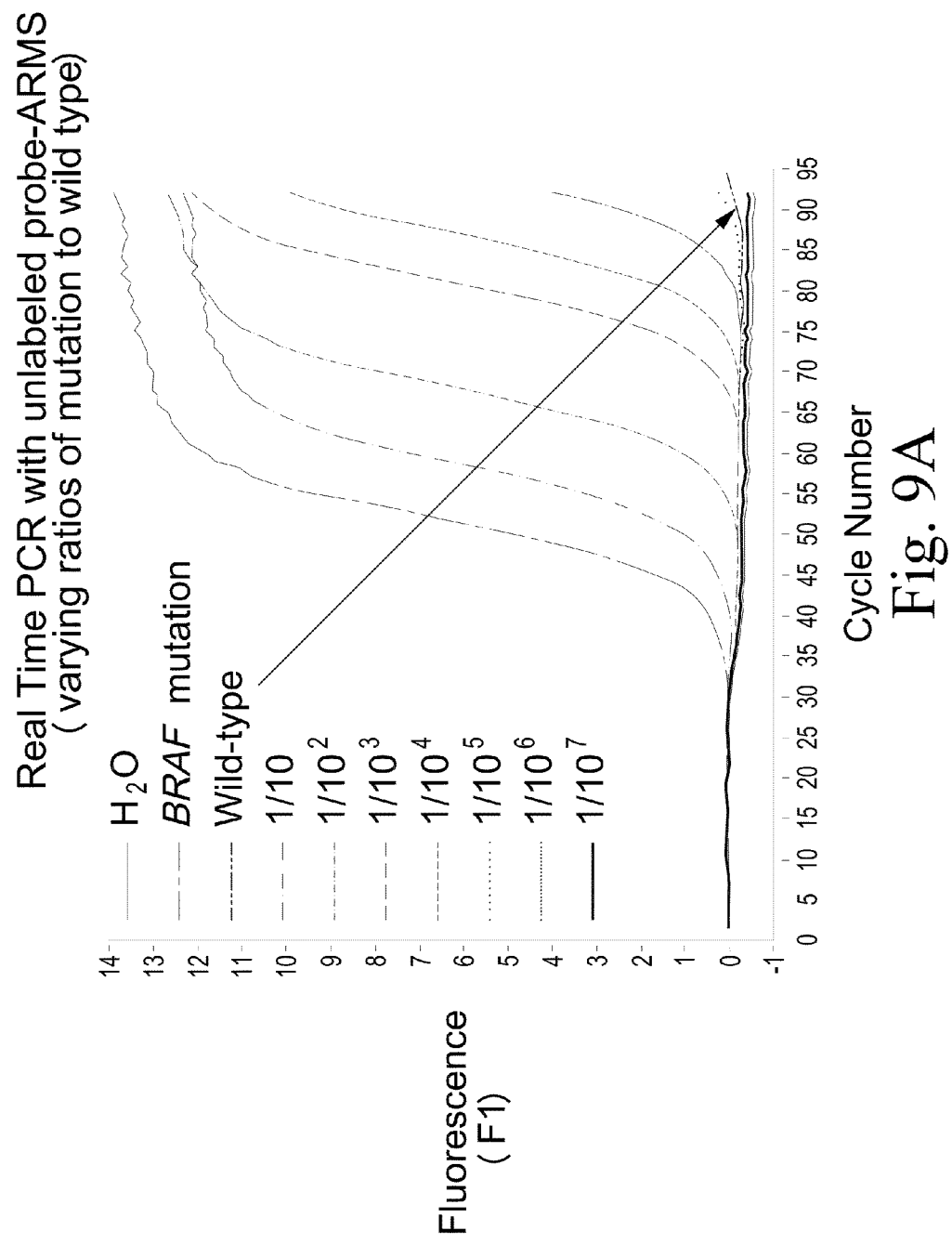
FIGS. 9A-B show real-time PCR with an ARMS primer combined with unlabeled probe to detect varying BRAF mutation to wild-type ratios.
Figure 9B:
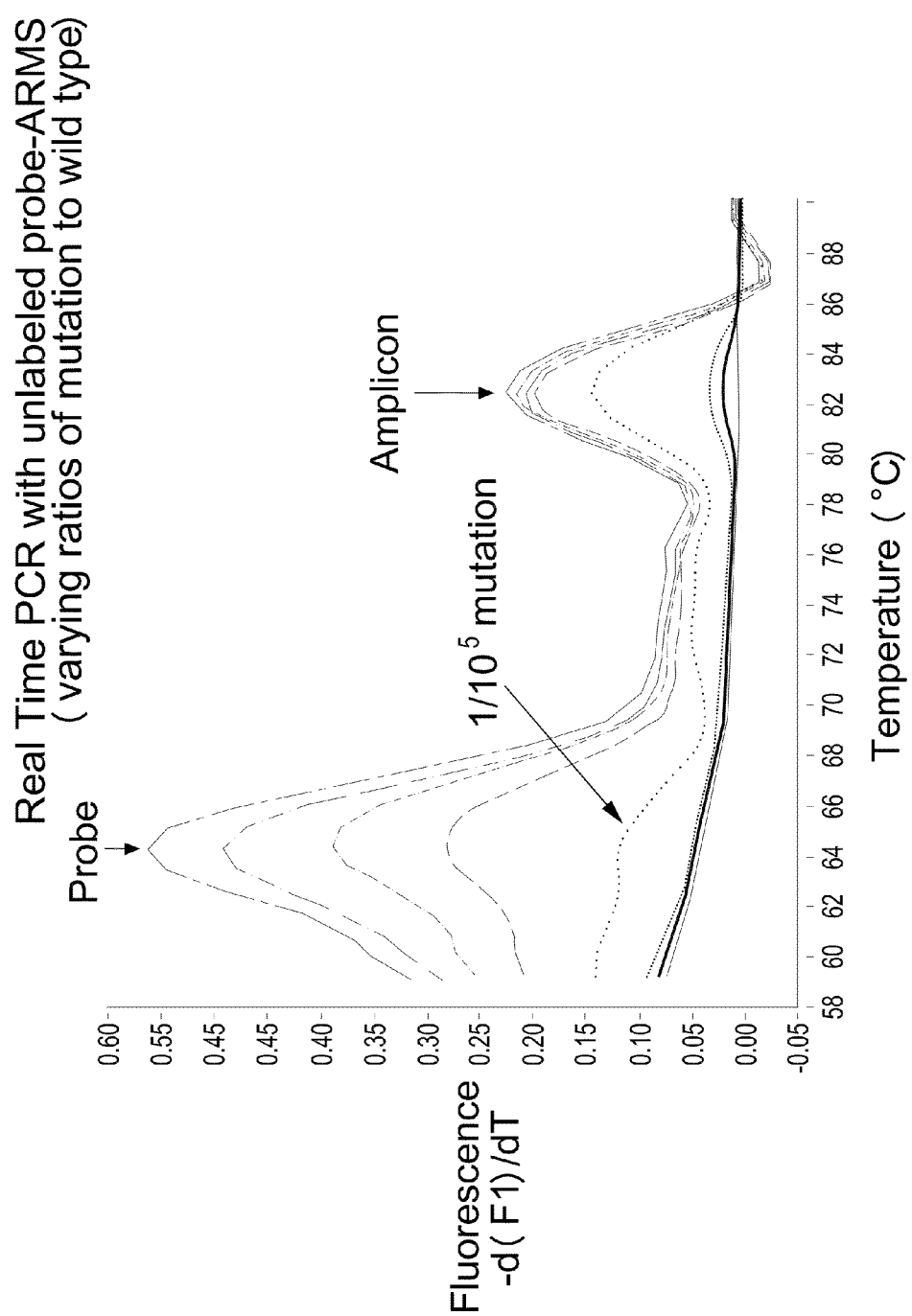

Because the molecular weight of human genomic DNA is high (660 g/mol), if the human genome copy number is up to $10^6$, the DNA is viscous and makes pipetting difficult. A 401 bp product, created from PCR, was used as the template for the initial study with the template covering the BRAF mutation T1796A. $10^6$ copies of mutation and wild-type were used for the ratios dilution. The ratios of BRAF mutation to wild-type were 1:10, 1:$10^2$, 1:$10^3$, 1:$10^4$, 1:$10^5$, 1:$10^6$ and 1:$10^7$. FIGS. 8A-B show the comparison of 10-fold ARMS asymmetric PCR without unlabeled probe. As seen in FIG. 8A, the detectable ratios of BRAF mutation to wild-type is 1:$10^4$ from amplification curves. The whole amplicon melting curve cannot distinguish the mutation from the wild-type (FIG. 8B). FIGS. 9A-B show real-time PCR with ARMS primer combined with unlabeled probe to detect varying BRAF mutation to wild-type ratios. The detectable ratios of BRAF mutation to wild-type is 1:105 from amplification curves (FIG. 9A) and probe melting curves (FIG. 9B). Unknown samples may be compared to such dilution series to quantify the amount of minor allele in a sample. This may be done by cycle number, as illustrated in FIG. 9A, or by peak height, as illustrated in FIG. 9B, or by other methods known in the art. By combining ARMS and unlabeled probe, the unlabeled probe not only blocks the wild-type but is also an indicator for the minor allele.

500 ng wild-type genomic DNA were used to mix with differing concentrations of BRAF mutation, with ratios of 1:10, 1:$10^2$, 1:$10^3$, 1:$10^4$, $10^5$ and $10^6$. The lowest detectable ratio of mutation to wild-type was 1:$10^5$ and the absolute mutation copy number was an average of 1.7 (data not shown).

Labeled probe-ARMS: The same principle as above is used but with combining ARMS and fluorescently labeled probes, such as HybProbes and molecular beacon probes, to enrich the minority allele. The HybProbes and molecular beacon probes were designed to anneal in the same region as the ARMS primer and match the wild-type. The ARMS primer selectively amplified the mutation and the probe was used to block the wild-type allele. 500 ng wild-type genomic DNA was used to mix different concentrations of BRAF mutation in ratios of 1:10, 1:10², 1:10³, 1:10⁴, 10⁵ and 10⁶. Combining HybProbe and ARMS, the lowest detectable ratio of mutation to wild-type was 1:10⁵. Combining the molecular beacon probe and ARMS, the lowest detectable ratio of mutation to wild-type was also 1:105, and possibly lower (data not shown).

Example 3

Probe-ARMS Enrichment for K-Ras Mutations

Twelve different forward primers, one common reverse primer, and one unlabeled probe were used to detect 12 K-ras mutations. The primers sequences for the K-ras mutations are shown in Table 1. The upper-case is the primer sequence. The lower case is a tail used to adjust the melting curve.

TABLE 1

Primer and probe sequences of K-ras codon 12 and 13

| Name | Forward primer | |
|---|---|---|
| K-ras12-1AF | TGTGGTAGTTGGAGCTA | (Seq. ID No. 9) |
| K-ras12-1CF | ccgcgatTGGTAGTTGGAGCTC | (Seq. ID No. 10) |
| K-ras12-1TF | ccgcTGTGGTAGTTGGAGCTT | (Seq. ID No. 11) |
| K-ras12-2AF | TGGTAGTTGGAGCTGA | (Seq. ID No. 12) |
| K-ras12-2CF | ccgcgatTGTAGTTGGAGCTGC | (Seq. ID No. 13) |
| K-ras13-1AF | TGGTAGTTGGAGCTGGTA | (Seq. ID No. 14) |
| K-ras13-1CF | ccgcgatTGTAGTTGGAGCTGGTC | (Seq. ID No. 15) |
| K-ras13-1TF | ccgcTGTGGTAGTTGGAGCTGGTT | (Seq. ID No. 16) |
| K-ras13-2AF | TGGTAGTTGGAGCTGGTGA | (Seq. ID No. 17) |
| K-ras13-2CF | ccgcgatTGTAGTTGGAGCTGGTGC | (Seq. ID No. 18) |
| K-ras13-2TF | ccgcTGTGGTAGTTGGAGCTGGTGT | (Seq. ID No. 19) |
| K-rasR | TCTCTATTGTTGGATCATATTC | (Seq. ID No. 20) |
| K-ras12-13-P | ccgcgTGTGGTAGTTGGAGCTGGTGGC-P | (Seq. ID No. 21) |

The mutations of interest for K-ras genotyping include three mutant alleles at one of four positions, two in codon 12, and two in codon 13, for a total of 12 mutant genotypes. These mutations occur in positions 1 and 2 in both codons, all of which have a G nucleotide in the wild-type allele, and so the mutant alleles exhibit either A, C, or T nucleotides in one of these positions, as shown in table 2.

TABLE 2

| | 12 13 | AA |
|---|---|---|
| Wild-type | GGTGGC | G12G |
| | AGTGGC | G12S |
| | CGTGGC | G12R |
| | TGTGGC | G12C |
| | GATGGC | G12D |
| | GCTGGC | G12A |

TABLE 2-continued

| | |
|---|---|
| GTTGGC | G12V |
| GGTAGC | G13S |
| GGTCGC | G13R |
| GGTTGC | G13C |
| GGTGAC | G13D |
| GGTGCC | G13A |
| GGTGTC | G13V |

For each of the four positions, we have designed there are four parallel sets of three ARMS primers whose 3' nucleotides match each mutant allele (the mutant nucleotide is underlined in Table 2), and a corresponding unlabeled probe whose nucleotide at the mutation position matches and blocks the wild-type allele, in a manner that when each set is combined with target DNA and PCR is performed, the primers will specifically amplify and enrich exactly the three K-ras genotypes with a mutation at the position for which they are designed. Two of each set of these primers are further designed to have differing length sequences of mismatched nucleotides inserted in their 5'-tails (tails shown in lower case in Table 1 above. FIG. 10 illustrates such a reaction with one variable nucleotide. As seen in FIG. 10, the primer for the "A" allele has no mismatched tail. The probe, which is configured to be a complete match for the wild-type, has a mismatch at the "A" nucleotide, and as configured in this example, there is an overhang between the probe and the "A" amplicon. The primer for the "C" allele is somewhat longer than the "A" primer, with a section that mismatches and loops out when the probe is bound. The "T" primer has a different tail that causes the probe to loop out. In the K-ras assays, for such sets of three primers were used, one set of three primers for each of the four variable positions. Tail length, loop size, GC content, and other sequence variations of the tail, as are know in the art, may be used to adjust the Tm of the probe-amplicon melting curve. It is understood that the exact configuration of the tails is not important, as long as the three primers have tails that are identifiable by melting curve or other means. Thus, any mutant allele that is amplified and enriched may be easily genotyped by the different melting temperatures exhibited by subsequent probe melting, as illustrated in FIGS. 11A-D. Using this technique, all 12 K-ras mutations can be easily, efficiently, economically and reliably detected and genotyped in only 4 reactions.

Thus, minority allele enrichment using ARMS combined with probe based genotyping methods the probe is not only suppress the wild-type but also is an indicator. The mutation detection sensitivity is 100 times high the use ARMS alone. Even a single molecule can be detectable in a high background of wild-type. Illustratively, no separation, purification or additional steps that increase risk of contamination and high-resolution melting are necessary.

Although the invention has been described in detail with reference to preferred embodiments, variations and modifications exist within the scope and spirit of the invention as described and defined in the following claims.

The invention claimed is:

1. A method for detecting a minor allele in a sample comprising,
   amplifying DNA comprising the minor allele and a major allele, wherein the minor allele is present in a lower concentration than the major allele, and the minor allele differs from the major allele by a nucleotide, wherein the amplifying step is performed using
      a pair of primers comprising an ARMS primer, wherein the ARMS primer is a Snapback ARMS primer, and a second primer, wherein a 3' terminal nucleotide of the ARMS primer is complementary to the nucleotide of the minor allele and is not complementary to the nucleotide of the major allele, and
      a probe, wherein the probe is a probe element located as a 5' end of the ARMS primer, wherein the probe has a nucleotide that is complementary to the nucleotide of the major allele and is not complementary to the minor allele, and
   detecting the minor allele using the probe under annealing or melting conditions.

2. The method of claim 1, wherein
   the amplifying step is performed using an additional Snapback ARMS primer, wherein the additional Snapback ARMS primer comprises a 3' nucleotide that matches a third allele and a probe element located at the 5' end that is different from the probe element of the Snapback ARMS primer, and
   the detecting step comprises generating a melt curve and determining whether the melt curve matches the 5' element of the Snapback ARMS primer or the 5' element of the additional Snapback ARMS primer.

3. The method of claim 1, wherein the ARMS primer is provided at a concentration of less than 0.5 μM.

4. The method of claim 3 wherein the ARMS primer is provided at a concentration of about 0.05 μM.

5. The method of claim 3, wherein the ARMS primer is provided at a concentration lower than the second primer.

6. The method of claim 5, wherein the second primer is provided at a concentration about 10 times of the ARMS primer.

7. The method of claim 1 wherein the amplifying step includes using an annealing temperature that is between a Tm of the minor allele and the probe and a Tm of the major allele and the probe.

* * * * *

UNITED STATES PATENT AND TRADEMARK OFFICE
CERTIFICATE OF CORRECTION

| | | |
|---|---|---|
| PATENT NO. | : 8,815,515 B1 | Page 1 of 1 |
| APPLICATION NO. | : 12/890041 | |
| DATED | : August 26, 2014 | |
| INVENTOR(S) | : Zhou | |

It is certified that error appears in the above-identified patent and that said Letters Patent is hereby corrected as shown below:

Title Page,
Add Item (60), Domestic Priority Data, --Provisional Application No. 61/245,352, filed on Sep. 24, 2009.--

Title Page 2, Right-hand column
Item (56), Other Publications, change "Detection fo Single Nucleotide" to --Detection for Single Nucleotide--

In the Specification

Column 3
Line 5, change "Research)" to --Research).--

Column 4
Line 13, change "perfectly matched and" to --perfectly matched probe and--

Figure 11A:
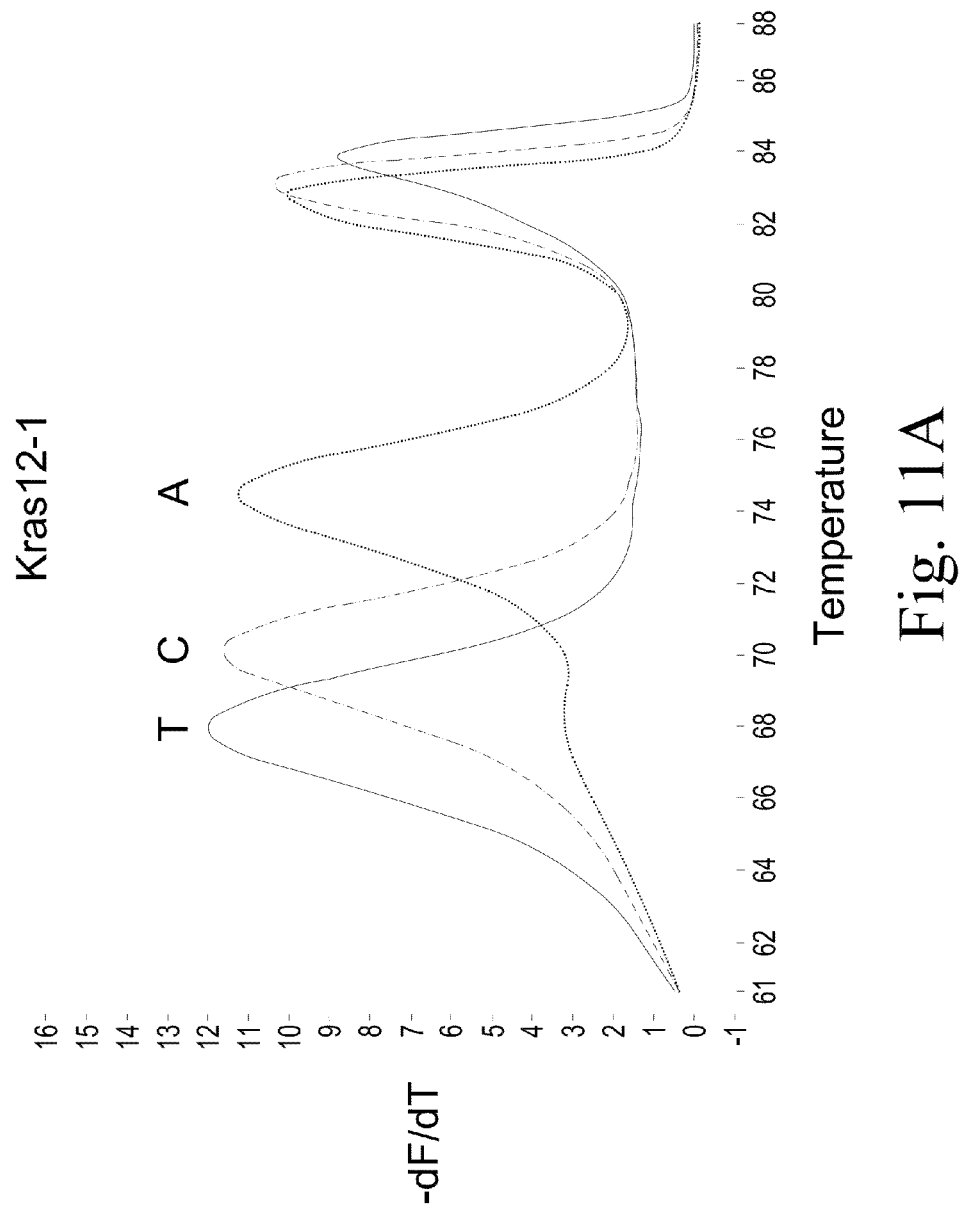
FIG. 11A-D shows derivative melting curves for each of the four K-ras nucleotides, using 5' tailed ARMS primers.
Figure 11B:
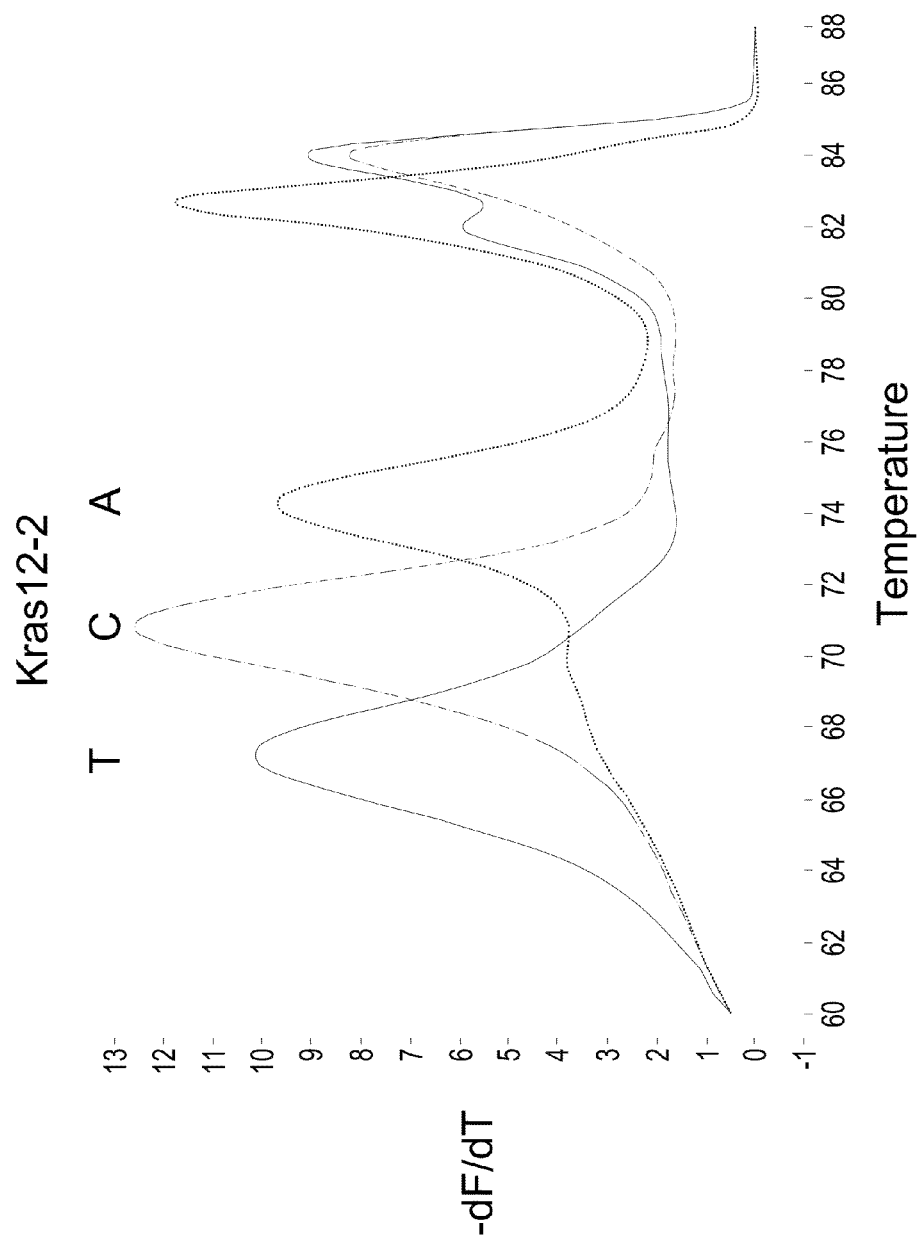
Figure 11C:
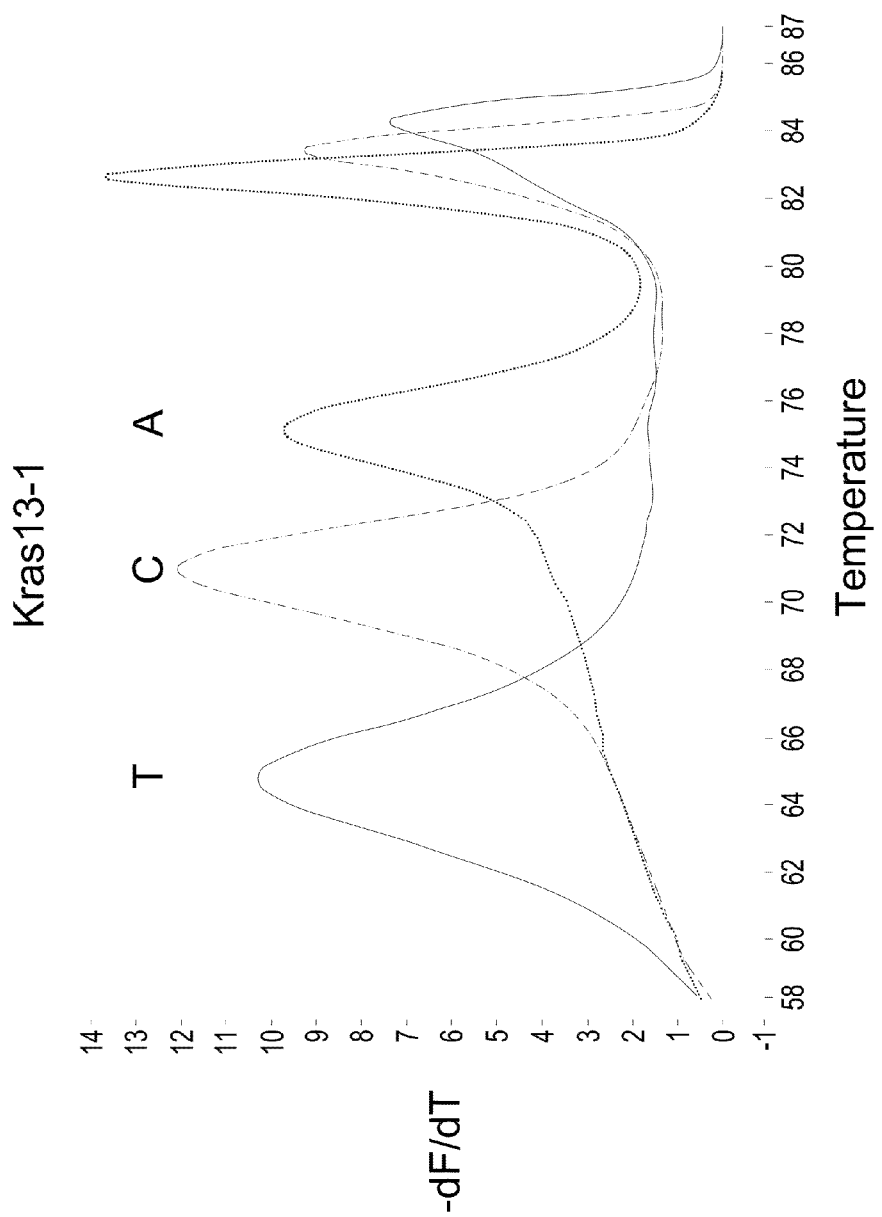
Figure 11D:
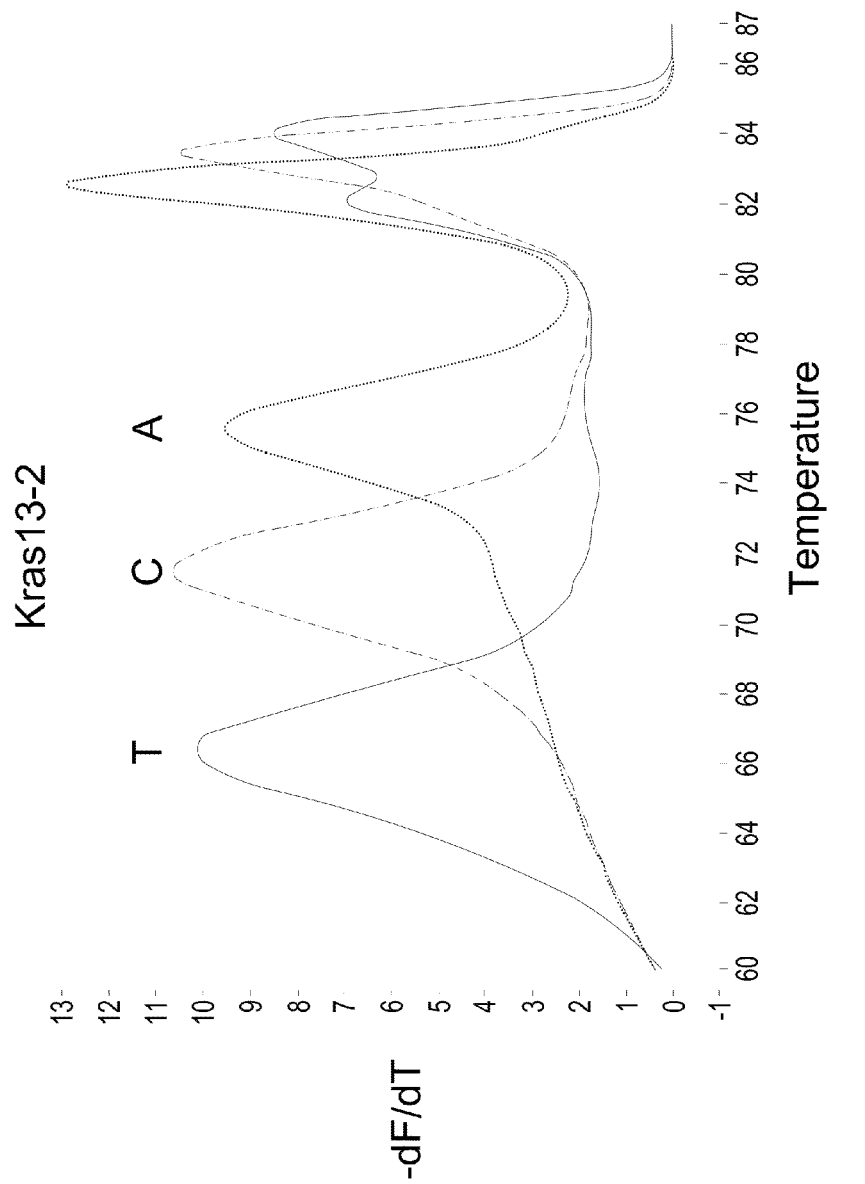

Column 5
Line 66, change "FIG. 11A" to --FIG 11D--

Signed and Sealed this
Tenth Day of March, 2015

Michelle K. Lee
*Deputy Director of the United States Patent and Trademark Office*